US012673992B2

(12) United States Patent
Cook et al.

(10) Patent No.:     US 12,673,992 B2
(45) Date of Patent:        *Jul. 7, 2026**

(54) BISPECIFIC ANTIBODIES AGAINST CD9 AND CD7

(71) Applicant: UCB BIOPHARMA SRL, Brussels (BE)

(72) Inventors: David Alan Cook, Slough (GB); Helen Margaret Finney, Slough (GB); Stephen Edward Rapecki, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 970 days.

This patent is subject to a terminal disclaimer.

(21) Appl. No.: 17/929,029

(22) PCT Filed: Feb. 13, 2020

(86) PCT No.: PCT/EP2020/053777
§ 371 (c)(1),
(2) Date: Aug. 10, 2022

(87) PCT Pub. No.: WO2021/160267
PCT Pub. Date: Aug. 19, 2021

(65) Prior Publication Data
US 2023/0096030 A1     Mar. 30, 2023

(51) Int. Cl.
*C07K 16/28*          (2006.01)

(52) U.S. Cl.
CPC ...... *C07K 16/2803* (2013.01); *C07K 2317/31* (2013.01); *C07K 2317/565* (2013.01); *C07K 2317/622* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 5,858,358 A | 1/1999 | June et al. | |
| 7,288,638 B2 | 10/2007 | Jure-Kunkel et al. | |
| 8,197,809 B2 * | 6/2012 | Park | A61P 35/00 |
| | | | 435/7.1 |
| 2011/0293579 A1 * | 12/2011 | Nielsen | A61P 19/02 |
| | | | 530/397 |
| 2017/0081404 A1 | 3/2017 | Finney et al. | |
| 2017/0355755 A1 | 12/2017 | Chen | |
| 2019/0330366 A1 | 10/2019 | Eckelman et al. | |

FOREIGN PATENT DOCUMENTS

| | | | |
|---|---|---|---|
| EP | 0336379 A2 | 10/1989 | |
| EP | 1532984 A1 | 5/2005 | |
| WO | 98/25967 A1 | 6/1998 | |
| WO | WO-03051926 A2 * | 6/2003 | ......... C07K 16/2803 |
| WO | 2005/035584 A1 | 4/2005 | |

| | | |
|---|---|---|
| WO | 2009/023955 A1 | 2/2009 |
| WO | 2014/028560 A2 | 2/2014 |
| WO | 2017/072183 A1 | 5/2017 |
| WO | 2017/119811 A1 | 7/2017 |
| WO | 2017/174331 A1 | 10/2017 |
| WO | 2018/114748 A1 | 6/2018 |
| WO | 2018/114754 A1 | 6/2018 |
| WO | 2018/187215 A1 | 10/2018 |
| WO | 2019/179391 A1 | 9/2019 |
| WO | 2021/160265 A1 | 8/2021 |
| WO | 2021/160266 A1 | 8/2021 |
| WO | 2021/160267 A1 | 8/2021 |
| WO | 2021/160268 A1 | 8/2021 |
| WO | 2021/160269 A1 | 8/2021 |

OTHER PUBLICATIONS

Runcie et al., Bi-specific and tri-specific antibodies—the next big thing in solid tumor therapeutics; 2018, Molecular Medicine, 24:50, pp. 1-15. (Year: 2018).*
Stillwell et al., T cell signal transduction and the role of CD7 in costimulation; 2001, Immunologic Research, 24(1): 31-52. (Year: 2001).*
Tai et al., A role for CD9 molecules in T cell activation; 1996, Journal of Experimental Medicine, 184: 753-758. (Year: 1996).*
Dahlén et al., "Bispecific antibodies in cancer immunotherapy," Therapeutic Advances in Vaccines and Immunotherapy 61(1):3-17 (2018).
Finney et al., "Activation of Resting Human Primary T cells with Chimeric Receptors: Costimulation from CD28, Inducible Costimulator, CD134, and CD137 in Series with Signals from the TCR Zeta Chain," The Journal of Immunology 172:104-113 (2004).
Huan et al., "Overexpression of CD9 correlates with tumor stage and lymph node metastasis in esophageal squamous cell carcinoma," Int J Clin Exp Pathol 8(3):3054-3061 (2015).
Hwang et al., "Upregulation of CD9 in ovarian cancer is related to the induction of TNF-alpha gene expression and constitutive NF-KB activation," Carcinogenesis 33(1):77-83 (2012).
Ikeyama et al., "Suppression of Cell Motility and Metastasis by Transfection with Human Motility-related Protein (MRP-1/CD9) DNA," J. Exp. Med. 177:1231-1237 (1993).
Kischel et al., "Overexpression of CD9 in Human Breast Cancer Cells Promotes the Development of Bone Metastases," Anticancer Research 32:5211-5220 (2012).
Liu et al., "Tumor-antigen expression-dependent activation of the CD137 costimulatory pathway by bispecific DART proteins," Retrieved from the Internet: URL:http://cancerres.aacrjournals.org/cont ent/77/13_Supplement/3642 (Jul. 1, 2017).
Makkouk et al, "Rationale for anti-CD137 cancer immunotherapy," European Journal of Cancer 54(1):112-119 (2016).
(Continued)

*Primary Examiner* — Nelson B Moseley, II
*Assistant Examiner* — James Ryland Melchior
(74) *Attorney, Agent, or Firm* — MEDLER FERRO WOODHOUSE & MILLS PLLC

(57) ABSTRACT

The present invention relates to multispecific antibodies against a novel targets' combination of CD7 and CD9, and their use in the treatment of cancer and infectious diseases.

15 Claims, 13 Drawing Sheets

Specification includes a Sequence Listing.

(56) References Cited

OTHER PUBLICATIONS

Masellis-Smith et al., "CD9-regulated adhesion. Anti-CD9 mono-clonal antibody induce pre-B cell adhesion to bone marrow fibro-blasts through de novo recognition of fibronectin.," The Journal of Immunology 152:2768-2777 (1994).

Murayama et al., "Novel CD9-targeted therapies in gastric cancer," World Journal of Gastroenterology 21 (11):3206-3213 (2015).

Nakamoto et al., "A novel therapeutic strategy with anti-CD9 antibody in gastric cancers," J Gastroenterol 44:889-896 (2009).

Park et al., "Anti-CD9 monoclonal antibody-stimulated invasion of endometrial cancer cell lines in vitro: possible Inhibitory effect of CD9 in endometrial cancer invasion," Molecular Human Repro-duction 6(8):719-725 (2000).

Rappa et al., "Tetraspanin CD9 determines invasiveness and tumorigenicity of human breast cancer cells," Oncotarget 6(10):7970-7991 (2015).

Reyes et al., "Tetraspanin CD9: A Key Regulator of Cell Adhesion in the Immune System," Frontiers in Immunology 9(863):1-9 (2018).

Sanchéz-Paulete et al., "Cancer Immunotherapy with Immunomodula-tory Anti-CD137 and Anti-PD-1 Monoclonal Antibodies Requires BATF3-Dependent Dendritic Cells," Cancer Discovery 71:71-99 (2015).

Segal et al., "Results from an Integrated Safety Analysis of Urelumab, an Agonist Anti-CD137 Monoclonal Antibody," Clinical Cancer Research 23(8):1929-1936 (2017).

Segal et al., "Phase I Study of Single-Agent Utomilumab (PF-05082566), a 4-1BB/CD137 Agonist, in Patients with Advanced Cancer," Clinical Cancer Research 24(8):1816-1823 (2018).

Tai et al., "A Role for CD9 Molecules in T Cell Activation," J. Exp. Med. 184(2):753-758 (1996).

International Search Report & Written Opinion, International Appli-cation No. PCT/EP2020/053771, Mailing Date: Oct. 16, 2020, 14 pages.

International Search Report & Written Opinion, International Appli-cation No. PCT/EP2020/053773, Mailing Date: Oct. 16, 2020, 10 pages.

International Search Report & Written Opinion, International Appli-cation No. PCT/EP2020/053780, Mailing Date: Nov. 23, 2020, 19 pages.

International Search Report & Written Opinion, International Appli-cation No. PCT/EP2020/053788, Mailing Date: Oct. 9, 2020, 12 pages.

Akbar et al., "The Effect of a Chimeric Mouse-Human CD7 Antibody on Human T, Natural Killer, and Lymphokine-Activated Killer Cell Activity In Vitro," Transplantation 52(2):325-350 (1991).

Flavell et al., "Characteristics and performance of a bispecific F (ab'y)2 antibody for delivering saporin to a CD7+ human acute T-cell leukaemia cell line", Br. J. Cancer 64:274-280 (1991).

Hoseini et al., "Acute myeloid leukemia targets for bispecific antibodies," Blood Cancer Journal 7(2):e522 (2017).

Kontermann et al., "Bispecific antibodies," Drug Discover Today 20(7):838-847 (2015).

Lazarovits et al., "CD7 is associated with CD3 and CD45 on human T cells," The Journal of Immunology 153(9):3956-3966 (1994).

Rabinowich et al., "Expression and function of CD7 molecule on human natural killer cells," The Journal of Immunology 152(2):517-526 (1994).

Sempowski et al., "Structure and Function of the CD7 Molecule," Critical Reviews in Immunology, CRC Press, Inc., US 19(4):331-348 (1999).

Tai et al., "CD9-mediated costimulation of TCR-triggered naive T cells leads to activation followed by apoptosis," The Journal of Immunology 159(8):3799-3807 (1997).

Toyo-Oka et al., "Synergy between CD28 and CD9 costimulation for naive T-cell activation," Immunology Letters, Elsevier BV, NL 58(1):19-23 (1997).

International Search Report, International Application No. PCT/EP2020/053777, Mailing Date: Oct. 20, 2020.

Non-final Office Action issued in U.S. Appl. No. 17/929,031 mailed Dec. 16, 2025.

* cited by examiner p=0.0065 p=0.0012

BISPECIFIC ANTIBODIES AGAINST CD9 AND CD7

FIELD OF THE INVENTION

The present invention belongs to the field of multispecific antibodies binding at least CD7 and CD9, and their uses in the treatment of cancer and/or infectious diseases.

BACKGROUND OF THE INVENTION

T cells are key to a successful cell-mediated immune response necessary to eliminate cancer cells, bacteria and viruses. They recognise antigens displayed on the surface of tumour cells or antigens from bacteria and viruses replicating within the cells or from pathogens or pathogen products endocytosed from the extracellular fluid. T cells have two major roles. They can become cytotoxic T cells capable of destroying cells marked as foreign. Cytotoxic T cells have a unique surface protein called CD8, thus they are often referred to as CD8+ T cells. Alternatively, T cells can become helper T cells, which work to regulate and coordinate the immune system. Helper T cells have a unique surface protein called CD4 and are thus often called CD4+ T cells. Helper T cells have several important roles in the immune system: 1) responding to activation by specific antigens by rapidly reproducing; 2) signaling B cells to produce antibodies; and 3) activating macrophages.

Cancer eludes the immune system by exploiting mechanisms developed to avoid auto-immunity. However, the immune system is programmed to avoid immune over-activation which could harm healthy tissue. T cell activation is at the core of these mechanisms. Antigen specific T cells normally able to fight disease can become functionally tolerant (exhausted) to infectious agents or tumour cells by over stimulation or exposure to suppressive molecules. Therefore, molecules that enhance the natural function of T cells or overcome suppression of T cells have great utility in the treatment or prevention of cancer and infectious disease.

In recent years, immunotherapy has become an established treatment option for an increasing number of cancer patients, exemplified by the increased use of therapeutic antibody-based immune checkpoint inhibitors (CPI's). This has arisen from an increased immunological understanding of how cancer cells perturb immune cell activation by hijacking pathways normally involved in maintaining tolerance and skewing the balance between co-stimulation and co-inhibition (Chen and Mellman., Immunity. 39:1-105 (2013)). Amongst the pathways that have emerged as key regulators in this regard, include CTLA-4 and the PD-1/PD-L1 checkpoint molecules serving to down-regulate T cell and myeloid cell activation in the tumour microenvironment. Ipilimumab (anti-CTLA-4) was the first CPI to be approved in 2011 as a treatment for melanoma, closely followed by FDA approval of anti-PD1 directed antibodies, pembrolizumab and nivolumab in 2014 (Hargadon et al., International Immunopharmacol. 62:29-39 (2018)). There are still significant challenges in understanding differences in efficacy across patient groups, ranging from complete responses, to treatment relapse and even failure to respond, (Haslam and Prasad. JAMA Network Open.5:2e192535 (2019)).

Despite the promising anti-tumour efficacy of several monoclonal antibodies, many cancers are refractory to treatments with a single antibody. Combinations of two or more antibodies are currently being tested in patients to provide improved methods of treatment. To date, these therapies rely on rational design of known mechanisms of action and are largely based on combining antigen-specificities known to be independently effective in the treatment of cancer, either as combination therapies or in a bispecific antibody format. This state of the art approach is a limiting factor in the development of new therapies as it relies on known therapies.

Therefore, there is still the need to identify novel modulators of T cell activation based on unbiased biology, which allows to identify novel target pairs capable of enhancing T cell activation and induction of T cell proliferation for the treatment of cancer and infectious diseases.

SUMMARY OF THE INVENTION

The present invention addresses the above-identified need by providing in a first aspect an antibody which comprises a first antigen-binding portion binding CD7 and a second antigen-binding portion binding CD9.

In one embodiment of this first aspect, each of the antigen-binding portions of the antibody which comprises a first antigen-binding portion binding CD7 and a second antigen-binding portion binding CD9 is a monoclonal antigen-binding portion.

In another embodiment, each of the antigen-binding portions is independently selected from a Fab, a Fab', a scFv or a VHH. In yet another aspect, the antigen-binding portions are the antigen-binding portions of an IgG.

In another embodiment, the antibody which comprises a first antigen-binding portion binding CD7 and a second antigen-binding portion binding CD9 is chimeric, human or humanised, and preferably the antibody is humanised.

In another embodiment, the antibody comprises a heavy chain constant region selected from an IgG1, an IgG2, IgG3 or an IgG4 isotype, or a variant thereof.

In another embodiment, the antibody further comprises at least an additional antigen-binding portion. The additional antigen-binding portion may be capable of increasing the half-life of the antibody. Preferably the additional antigen-binding portion binds albumin, more preferably human serum albumin.

In one embodiment, the first antigen binding portion binds CD7 and/or the second antigen binding portion binds CD9 in CD9 loop 2, wherein preferably the second antigen-binding portion binds within amino acids 112 to 195 of SEQ ID NO: 2.

In another embodiment, the first antigen-binding portion binding CD7 of the antibody according to the invention comprises a first heavy chain variable region and a first light chain variable region and the second antigen-binding portion binding CD9 comprises a second heavy chain variable region and a second light chain variable region and wherein:

a. The first heavy chain variable region comprises a CDR-H1 comprising SEQ ID NO: 3, a CDR-H2 comprising SEQ ID NO: 4 and a CDR-H3 comprising SEQ ID NO: 5; and b. The first light chain variable region comprises a CDR-L1 comprising SEQ ID NO: 6, a CDR-L2 comprising SEQ ID NO: 7 and a CDR-L3 comprising SEQ ID NO: 8; and c. The second heavy chain variable region comprises a CDR-H1 comprising SEQ ID NO: 9, a CDR-H2 comprising SEQ ID NO: 10 and a CDR-H3 comprising SEQ ID NO: 11; and d. The second light chain variable region comprises a CDR-L1 comprising SEQ ID NO: 12, a CDR-L2 comprising SEQ ID NO: 13 and a CDR-L3 comprising SEQ ID NO: 14;

or e. The first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21;

or f. The first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

In a second aspect of the present invention there is provided a pharmaceutical composition comprising the antibody according to the first aspect of the invention and all its embodiments and one or more pharmaceutically acceptable excipients.

In a third aspect, the invention provides for the antibody according to the first aspect of the invention and all its embodiments or the pharmaceutical composition according to the second aspect of the invention and all its embodiments for use in therapy.

In one embodiment of this third aspect, the use is for the treatment of cancer and/or an infectious disease. In another embodiment, the antibody or the composition according to the invention and all its embodiments are for use in the treatment of cancer concomitantly or sequentially to one or more additional cancer therapies.

In a fourth aspect of the present invention, there is provided for a method for treating a subject afflicted with cancer and/or an infectious disease, comprising administering to the subject a pharmaceutically effective amount of the antibody according to the first aspect of the invention and all its embodiments or the pharmaceutical composition according to the second aspect of the invention and all its embodiments.

In one embodiment of this fourth aspect, the antibody or the composition are administered concomitantly or sequentially to one or more additional cancer therapies.

In a fifth aspect, the invention provides for the use of an antibody according to the first aspect of the invention and all its embodiments or the pharmaceutical composition according to the second aspect of the invention and all its embodiments in the manufacture of a medicament for treating cancer.

In one embodiment of this fifth aspect, the antibody or the composition are administered concomitantly or sequentially to one or more additional cancer therapies.

DETAILED DESCRIPTION OF THE INVENTION

Figure 1:
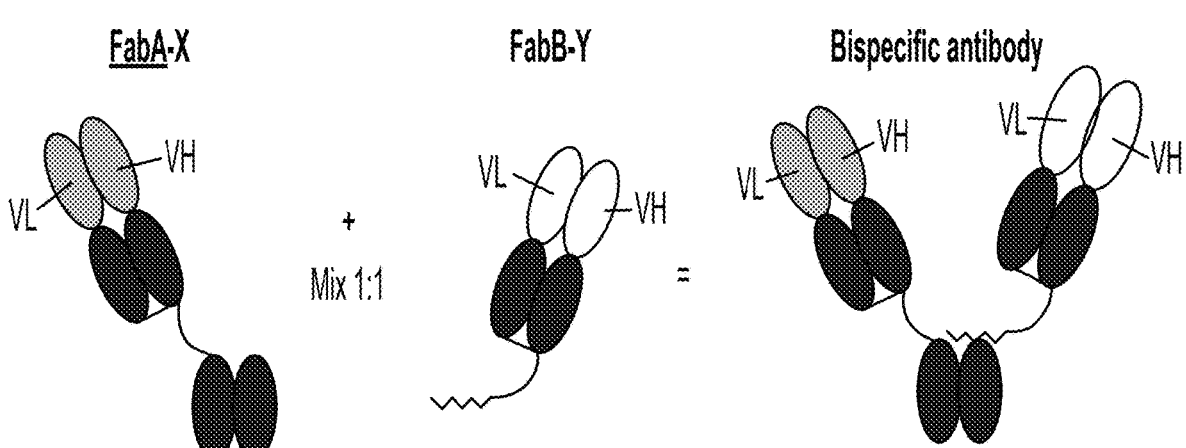
FIG. 1. General representation of a Fab-X and Fab-Y comprising antigen-binding portions and of the resulting bispecific antibody.

The present invention will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject, i.e. a human, which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of antibody comprising the distinct antigen-binding portions binding CD7 and CD9 that, when administered to a mammal or other subject for treating a disease, is sufficient to affect such treatment for the disease.

The present invention provides for antibodies comprising a first antigen-binding portion binding CD7 and a second antigen-binding portion binding CD9. The first and the second antigen-binding portions are located in the same antibody, i.e. they are part of the same polypeptide chain and/or associate via one or more covalent and/or non-covalent associations (such as the screening format Fab-Kd-Fab described herein or the classic heavy and light chain association forming a full IgG antibody) or are covalently linked so as to form one single molecule (such as cross-linking two separately expressed polypeptide chains, optionally via specific cross-linking agents).

CD7 and in particular human CD7 (Uniprot accession number P09564) is a transmembrane protein which is a member of the immunoglobulin superfamily. This protein is found on thymocytes and mature T cells. It plays an essential role in T cell signal transduction, T cell interactions and also in T cell/B cell interaction during early lymphoid development (Immunologic Research 24, 31-52 (2001)). The sequence of human CD7, including the signal peptide is shown as SEQ ID NO:1 (Table 1).

CD9 and in particular human CD9 (Uniprot accession number P21926) was discovered as a human B lymphocyte differentiation antigen and it has been found to be widely expressed on many non-hematopoietic tissues including various cancer. It is also known as Tetraspanin-29, motility-related protein-1, 5H9 antigen, cell growth-inhibiting gene 2 protein, leukocyte antigen MIC3 and MRP-1 (Rappa et al., Oncotarget 6:10, 7970-7991 (2015)). CD9 is a tetraspanin that is broadly expressed in a variety of solid tissues and on a multitude of hematopoietic cells (Nature reviews Cancer (9) 40-55 (2009)). CD9 involvement has been shown in the invasiveness and tumorigenicity of human breast cancer cells (Oncotargets, 6:10 (2015)), the suppression of cell motility and metastasis (J. Exp. Med 177:5 (1993)) and to have a role in T cell activation (J. Exp. Med 184:2 (1994)).

CD9 has also been shown to be present in exosomes (Asia-Pac J Clin Oncol, 2018; 1-9). Exosomes are cell derived nanovesicles with size of 30-120 nm. The molecular composition of exosomes reflects their origin and include unique composition of tetraspanins. Exosomes are thought to constitute a potent mode of intercellular communication that is important in the immune response, cell-to-cell spread of infectious agents, and tumour progression.

The sequence of human CD9, including the signal peptide is shown as SEQ ID NO:1 (Table 1).

TABLE 1

| SEQ ID NO: 1 Human CD7 | MAGPPRLLLLPLLLALARGLPGALAAQEVQQ SPHCTTVPVGASVNITCSTSGGLRGIYLRQL GPQPQDIIYYEDGVVPTTDRRFRGRIDFSGS QDNLTITMHRLQLSDTGTYTCQAITEVNVYG SGTLVLVTEEQSQGWHRCSDAPPRASALPAP PTGSALPDPQTASALPDPPAASALPAALAVI SFLLGLGLGVACVLARTQIKKLCSWRDKNSA ACVVYEDMSHSRCNTLSSPNQYQ |
|---|---|
| SEQ ID NO: 2 Human CD9 | MPVKGGTKCIKYLLFGFNFIFWLAGIAVLAI GLWLRFDSQTKSIFEQETNNNNSSFYTGVYI LIGAGALMMLVGFLGCCGAVQESQCMLGLFF GFLLVIFAIEIAAAIWGYSHKDEVIKEVQEF YKDTYNKLKTKDEPQRETLKAIHYALNCCGL AGGVEQFISDICPKKDVLETFTVKSCPDAIK EVFDNKFHIIGAVGIGIAVVMIFGMIFSMIL CCAIRRNREMV |
| SEQ ID NO: 3 CDR-H1 VR8850 | GFSLSSFAMC |
| SEQ ID NO: 4 CDR-H2 VR8850 | IINTGGSAYYASWATG |
| SEQ ID NO: 5 CDR-H3 VR8850 | GNGYAGYGYDGFDP |
| SEQ ID NO: 6 CDR-L1 VR8850 | QASQSITSWLS |
| SEQ ID NO: 7 CDR-L2 VR8850 | AASKLTF |
| SEQ ID NO: 8 CDR-L3 VR8850 | QSNYGSSSAYGA |
| SEQ ID NO: 9 CDR-H1 VR7270 | GFSLSSYAMG |
| SEQ ID NO: 10 CDR-H2 VR7272 | AIGSITATGYARWAKG |
| SEQ ID NO: 11 CDR-H3 VR7272 | EIYVGSAYAFDI |
| SEQ ID NO: 12 CDR-L1 VR7272 | QASQSISNYLA |
| SEQ ID NO: 13 CDR-L2 VR7272 | LASTLAS |
| SEQ ID NO: 14 CDR-L3 VR7272 | QQGYIDNVNKG |

8

TABLE 1-continued

| SEQ ID NO: 15 VH VR8850 | QSVEESGGRLVTPGTPLTLTCTVSGFSLSSF AMCWVRQAPGKGLEYIGIINTGGSAYYASWA TGRFTISKTSTTVDLKISSPTTEDTATYFCA RGNGYAGYGYDGFDPWGPGTLVTVSS |
|---|---|
| SEQ ID NO: 16 VH nucl. VR8850 | AAGCTTCGAAGCCACCATGGAGACTGGGCTG CGCTGGCTTCTCCTGGTCGCTGTGCTCAAAG GTGTCCAGTGTCAGTCGGTGGAGGAGTCCGG GGGTCGCCTGGTCACGCCGGGGACACCCCTG ACACTCACCTGCACAGTCTCTGGATTCTCCC TCAGTAGCTTTGCAATGTGCTGGGTCCGCCA GGCTCCAGGGAAGGGACTGGAATACATCGGA ATCATTAATACTGGTGGTAGCGCATACTACG CGAGCTGGGCGACAGGCCGATTCACCATCTC CAAAACCTCGACCACGGTGGATCTGAAAATC TCCAGTCCGACAACCGAGGACACGGCCACCT ATTTCTGTGCCAGAGGAAATGGTTATGCTGG TTATGGTTATGATGGTTTTGATCCCTGGGGC CCAGGCACCCTGGTCACCGTCTCGAGT |
| SEQ ID NO: 17 VL VR8850 | DIVMTQTPASVSEPVGGTVTIKCQASQSITS WLSWYQQKPGQPPKKLIYAASKLTFGVSSRF RGSGSGTEYTLTISDLECADAATYYCQSNYG SSSAYGAFGGGTEVVVK |
| SEQ ID NO: 18 VL nucl. VR8850 | AAGCTTCGAAGCCACCATGGACACGAGGGCC CCCACTCAGCTGCTGGGGCTCCTGCTGCTCT GGCTCCCAGGTGCCAGATGTGCTGACATTGT GATGACCCAGACTCCAGCCTCCGTGTCTGAA CCTGTGGGAGGCACAGTCACCATCAAGTGCC AGGCCAGTCAGAGCATTACCAGTTGGTTATC CTGGTATCAGCAGAAACCAGGGCAGCCTCCC AAGCTCCTGATCTACGCGGCATCCAAACTGA CATTTGGGGTCTCATCAAGATTCAGAGGCAG TGGATCTGGGACAGAGTACACTCTCACCATC AGCGACCTGGAGTGTGCCGATGCTGCCACTT ACTACTGTCAAAGCAATTATGGTAGTAGTAG TGCTTATGGGGCTTTCGGCGGAGGGACCGAG GTGGTGGTCAAACGTACG |
| SEQ ID NO: 19 VH VR7272 | QSLEESGGRLVTPGTPLTLTCTVSGFSLSSY AMGWVRQAPGKGLEWIGAIGSITATGYARWA KGRFSISKTSTTVDLKMTSPTTEDTATYFCA REIYVGSAYAFDIWGPGTLVTVSS |
| SEQ ID NO: 20 VH nucl. VR7272 | AAGCTTCGAAGCCACCATGGAGACTGGGCTG CGCTGGCTTCTCCTGGTCGCTGTGCTCAAAG GTGTCCAGTGTCAGTCGCTGGAGGAGTCCGG GGGTCGCCTGGTCACGCCTGGGACACCCCTG ACACTCACCTGCACAGTCTCTGGATTCTCCC TCAGTAGCTATGCAATGGGCTGGGTCCGCCA GGCTCCAGGGAAGGGGCTGGAGTGGATCGGA GCCATTGGTAGTATTACTGCCACTGGCTACG CGCGCTGGGCAAAAGGCCGATTCAGCATCTC CAAGACCTCGACCACGGTGGATCTGAAAATG ACCAGTCCGACAACCGAGGACACGGCCACCT ATTTCTGTGCCAGAGAGATTTATGTTGGGTC TGCTTATGCCTTTGACATCTGGGGCCCAGGC ACCCTGGTCACCGTCTCGAGT |
| SEQ ID NO: 21 VL VR7272 | AYDMTQTPASVEVAVGDTVTIKCQASQSISN YLAWYQQKPGQPPKLLIYLASTLASGVPSRF KGSGSGTEFTLTISDLECADAATYYCQQGYI DNVNKGFGGGTEVVVK |
| SEQ ID NO: 22 VL nucl. VR7272 | AAGCTTCGAAGCCACCATGGACACGAGGGCC CCCACTCAGCTGCTGGGGCTCCTGCTGCTCT GGCTCCCAGGTGCCAGATGTGCCTATGATAT GACCCAGACTCCAGCCTCTGTGGAGGTAGCT GTGGGAGACACTGTCACCATCAAGTGTCAGG CCAGTCAGAGCATTAGTAACTACTTAGCCTG GTATCAGCAGAAACCAGGGCAGCCTCCCAAG CTCCTGATCTATCTGGCATCTACTCTGGCAT CTGGGGTCCCATCGCGGTTCAAAGGCAGTGG ATCTGGGACAGAGTTCACTCTCACCATCAGC GACCTGGAGTGTGCCGATGCTGCCACTTACT ATTGTCAACAGGGTTATATTGATAATGTTAA TAAAGGTTTCGGCGGAGGGACCGAGGTGGTG GTCAAACGTACG |

Within the present invention, unless recited otherwise, human CD7 and CD9 are always intended to be included in the term "CD7" and "CD9". However, unless "human CD7" and/or "human CD9" are explicitly used, the terms "CD7" and/or "CD9" include the same targets in other species, especially non-primate (e.g. rodents) and non-human primate (such as cynomolgus monkey) species.

The present invention therefore provides for an antibody comprising a first antigen-binding portion binding human CD7 and a second antigen-binding portion binding human CD9. The first and the second antigen-binding portions are located on the same antibody, i.e. they are part of the same polypeptide chain, they associate via one or more non-covalent and/or covalent associations or are linked so as to form one single molecule.

The present invention also provides for an antibody comprising a first antigen-binding portion binding an extracellular domain region of human CD7 and a second antigen-binding portion binding an extracellular domain region of human CD9.

In particular, the present invention provides for an antibody comprising a first antigen-binding portion binding human CD7 as defined in SEQ ID NO: 1 or from amino acid 26 to 240 of SEQ ID NO: 1 or from amino acid 26 to 180 of SEQ ID NO:1 and a second antigen-binding portion binding human CD9 as defined in SEQ ID NO: 2 or from amino acid 2 to 228 of SEQ ID NO: 2, alternatively from amino acid 34 to 55 of SEQ ID NO: 2 or preferably the second antigen-binding portion binds within amino acid 112-195 of SEQ ID NO: 2. The first and the second antigen-binding portions are located on the same antibody, i.e. they are part of the same polypeptide chain, they associate via one or more non-covalent and/or covalent associations or are linked so as to form one single molecule.

The monoclonal antibody of the present invention, upon binding of CD7 and CD9, activates T cells and enhances induction of T cell proliferation and cytokine production, and in particular, the monoclonal antibody comprising a first antigen-binding portion binding CD7 and a second antigen-binding portion biding CD9 further activates T cells and enhances induction of T cell proliferation in the presence of an anti-CD3 stimulation or in the presence of *Staphylococcus aureus* Enterotoxin B (SEB). More specifically, the monoclonal antibody comprising a first antigen-binding portion binding CD7 and a second antigen-binding portion binding CD9 enhances cytokine production and enhances induction of T cell proliferation in the presence of an anti-CD3 stimulation or a SEB stimulation, but it does not activate unstimulated T cells. More specifically, the T cell is at least a CD4+ T cell or at least a CD8+ T cell or a mixture thereof.

The term "activate" (and grammatical variations thereof) as used herein at least includes the upregulation of specific cytokines, i.e. increased transcription and/or translation of these cytokines and/or release/secretion of these cytokines.

Hence, the present invention provides for a monoclonal antibody comprising a first antigen-binding portion binding CD7 and a second antigen-binding portion binding CD9 capable of activating T cells in the presence of a super antigen as SEB or an anti-CD3 stimulation wherein the further activation of T cell is measured as an upregulation or enhancement of cytokines production and the enhancement of T cell proliferation.

Upregulation or enhancement of cytokines production includes but is not limited to the upregulation of granzyme B and/or interferon gamma (IFNgamma).

In one preferred embodiment of the present invention, the monoclonal antibody comprising a first antigen-binding portion binding CD7 and a second antigen-binding portion binding CD9 is capable of upregulating or enhancing cytokines production and/or enhancing T cell proliferation in the presence of a super antigen such as SEB or an anti-CD3 stimulation wherein upregulating or enhancing cytokines production results in an upregulation of granzyme B and/or IFNgamma.

The term "antibody" as used herein include whole immunoglobulin molecules and antigen-binding portions of immunoglobulin molecules associated via non-covalent and/or covalent associations or linked together, optionally via a linker.

In one embodiment, the antigen-binding portions binding CD7 and CD9 are the antigen-binding portions of an IgG, wherein one arm binds CD7 and the other arm binds CD9.

In another embodiment, the antigen-biding portions comprised in the antibody are functionally active fragments or derivatives of a whole immunoglobulin and may be, but are not limited to, VH, VL, VHH, Fv, scFv fragment (including dsscFv), Fab fragments, modified Fab fragments, Fab' fragments, F(ab')$_2$ fragments, Fv and epitope-binding fragments of any of the above.

Other antibody fragments include those described in WO2005003169, WO2005003170, WO2005003171, WO2009040562 and WO2010035012. Functionally active fragments or derivative of a whole immunoglobulin and methods of producing them are well known in the art, see for example Verma et al., 1998, Journal of Immunological Methods, 216, 165-181; Adair and Lawson, 2005. Therapeutic antibodies. Drug Design Reviews—Online 2(3):209-217.

In one embodiment of the invention each of the antigen-binding portion is independently selected from a Fab, a Fab', a scFv or a VHH. In one embodiment, the antigen-binding portion binding CD7 is a Fab whilst the antigen-binding portion binding CD9 is a scFv. In another embodiment, the antigen-binding portion binding CD9 is a Fab whilst the antigen-binding portion binding CD7 is a scFv. In another embodiment, both antigen-binding portions are a Fab or scFv.

In one preferred embodiment, the antibody is monoclonal, which means that the antigen-binding portions comprised therein are all monoclonal. Therefore, in one preferred embodiment of the present invention, there is provided a monoclonal antibody comprising a first antigen-binding portion binding CD7 and a second antigen-binding portion binding CD9. Preferably, this antibody is capable of upregulating or enhancing cytokines production and/or enhancing induction of T cell proliferation in the presence of a super antigen such as SEB or an anti-CD3 stimulation wherein upregulating or enhancing cytokines production results in an upregulation of granzyme B and/or IFNgamma.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by

11

Babcook, J. et al, 1996, Proc. Natl. Acad. Sci. USA 93(15): 7843-78481; WO92/02551; WO2004/051268 and WO2004/106377.

The antibodies of the present invention can also be generated using various phage display methods known in the art and include those disclosed by Brinkman et al. (in J. Immunol. Methods, 1995, 182: 41-50), Ames et al. (J. Immunol. Methods, 1995, 184: 177-186), Kettleborough et al. (Eur. J. Immunol. 1994, 24:952-958), Persic et al. (Gene, 1997 187 9-18), Burton et al. (Advances in Immunology, 1994, 57: 191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. When the antigen-binding portions comprised in the antibody are functionally active fragments or derivatives of a whole immunoglobulin such as single chain antibodies, they may be made such as those described in U.S. Pat. No. 4,946,778 which can also be adapted to produce single chain antibodies binding to CD7 and CD9. Transgenic mice, or other organisms, including other mammals, may be used to express antibodies, including those within the scope of the invention.

The antibody of the present invention may be chimeric, human or humanised.

Chimeric antibodies are those antibodies encoded by immunoglobulin genes that have been genetically engineered so that the light and heavy chain genes are composed of immunoglobulin gene segments belonging to different species.

Humanized, antibodies are antibody molecules from non-human species having one or more complementarity determining regions (CDRs) from the non-human species and a framework region from a human immunoglobulin molecule (see, e.g. U.S. Pat. No. 5,585,089; WO91/09967). Preferably the antibody of the present invention is humanized. In one embodiment of the present invention, there is provided an antibody, preferably a monoclonal antibody, comprising a first antigen-binding portion binding CD7 and a second antigen-binding portion binding CD9, wherein the antibody is humanised. More preferably this antibody is capable of upregulating or enhancing cytokines production and/or enhancing T cell proliferation and/or enhancing induction of T cell proliferation in the presence of an anti-CD3 stimulation wherein upregulating or enhancing cytokines production results in an upregulation of granzyme B and/or IFN-gamma.

In humanized antibodies, the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment, rather than the entire CDR being transferred, only one or more of the specificity determining residues from any one of the CDRs described herein above are transferred to the human antibody framework (see, for example, Kashmiri et al., 2005, Methods, 36, 25-34). In one embodiment, only the specificity determining residues from one or more of the CDRs described herein above are transferred to the human antibody framework. When the CDRs or specificity determining residues are grafted, any appropriate acceptor variable region framework sequence may be used having regard to the class/type of the donor antibody from which the CDRs are derived, including mouse, primate and human framework regions. Preferably, the humanized antibody according to the invention comprises a variable domain comprising human acceptor framework regions as well as one or more of the CDRs or specificity determining residues described above. Thus, provided in one embodiment is a humanized monoclonal antibody comprising an antigen-binding portion binding CD7 and an antigen-binding portion binding CD9, wherein each antigen-binding portion comprises a variable domain comprising human acceptor framework regions and non-human donor CDRs.

Examples of human frameworks which can be used in the invention are KOL, NEWM, REI, EU, TUR, TEI, LAY and POM (Kabat et al, supra). For example, KOL and NEWM can be used for the heavy chain, REI can be used for the light chain and EU, LAY and POM can be used for both the heavy chain and the light chain. Alternatively, human germline sequences may be used; these are available at, for example: http://vbase.mrc-cpe.cam.ac.uk/. In a CDR-grafted antibody of the invention, the acceptor heavy and light chains do not necessarily need to be derived from the same antibody and may, if desired, comprise composite chains having framework regions derived from different chains.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts, e.g., as described in general terms in EP0546073, U.S. Pat. Nos. 5,545,806, 5,569,825, 5,625,126, 5,633,425, 5,661,016, 5,770,429, EP 0438474 and EP0463151.

Furthermore, the antibody of the invention may comprise a heavy chain constant region selected from an IgG1, an IgG2, an IgG3 or an IgG4 isotype, or a variant thereof. The constant region domains of the antibody of the invention, if present, may be selected having regard to the proposed function of the antibody, and in particular the effector functions which may be required. For example, the human IgG constant region domains of the IgG1 and IgG3 isotypes may be used when the antibody effector functions are required. Alternatively, IgG2 and IgG4 isotypes may be used when the antibody effector functions are not required. For example, IgG4 molecules in which the serine at position 241 has been changed to proline as described in Angal et al., Molecular Immunology, 1993, 30 (1), 105-108 may be used. Particularly preferred is the IgG4 constant domain that comprises this change.

It should also be appreciated that antigen-binding portions comprised in the antibody of the invention such as the functionally-active fragments or derivatives of a whole immunoglobulin fragments described above, may be incorporated into other antibody formats than being the antigen-binding portions of the classic IgG format. Alternative format to the classic IgG may include those known in the art and those described herein, such as DVD-Igs, FabFvs for example as disclosed in WO2009/040562 and WO2010/035012, diabodies, triabodies, tetrabodies etc. Other examples include a diabody, triabody, tetrabody, bibodies and tribodies (see for example Holliger and Hudson, 2005, Nature Biotech 23(9): 1 126-1136; Schoonjans et al. 2001, Biomolecular Engineering, 17 (6), 193-202), tandem scFv, tandem scFv-Fc, FabFv, Fab'Fv, FabdsFv, Fab-scFv, Fab'-scFv, diFab, diFab', scdiabody, scdiabody-Fc, ScFv-Fc-scFv, scdiabody-CH3, IgG-scFv, scFv-IgG, V-IgG, IgG-V, DVD-Ig, DuoBody, Fab-Fv-Fv, Fab-Fv-Fc and Fab-dsFv-PEG fragments described in WO2009040562, WO2010035012, WO2011/08609, WO2011/030107 and WO2011/061492, respectively.

Furthermore, the antibody of the invention may comprise along with the antigen-binding portions binding CD7 and CD9, also at least an additional antigen-binding portion. Therefore, in one embodiment, there is provided an antibody, preferably a monoclonal antibody, comprising a first antigen-binding portion binding CD7 and a second antigen-binding portion binding CD9, wherein the antibody is humanised and wherein the antibody further comprises an additional antigen-binding portion. More preferably this antibody is capable of upregulating or enhancing cytokines production and/or enhancing T cell proliferation and/or enhancing induction of T cell proliferation. The stimulation may be an anti-CD3 stimulation wherein upregulating or enhancing cytokines production results in an upregulation of granzyme B and/or IFNgamma.

In one embodiment, the additional antigen-binding portion is capable of increasing, i.e. extending, the half-life of the antibody. Preferably, the additional antigen-binding portion binds albumin, more preferably human serum albumin.

In one preferred embodiment, the antibody comprises a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

The antibody of the present invention may be comprised in a pharmaceutical composition along with one or more pharmaceutically acceptable excipients. By pharmaceutical composition is intended a composition for both therapeutic and diagnostic use. In another aspect, the present invention provides for a pharmaceutical composition comprising an antibody, preferably a monoclonal antibody, comprising a first antigen-binding portion binding CD7 and a second antigen-binding portion binding CD9, wherein the antibody is preferably humanised and wherein the composition comprises one or more pharmaceutically acceptable excipients.

Pharmaceutically acceptable excipients in therapeutic compositions may additionally contain liquids such as water, saline, glycerol and ethanol. Additionally, auxiliary substances, such as wetting or emulsifying agents or pH buffering substances, may be present in such compositions. Such excipients enable the pharmaceutical compositions to be formulated as tablets, pills, dragees, capsules, liquids, gels, syrups, slurries and suspensions, for ingestion by the patient.

The antibody of the present invention and the pharmaceutical composition comprising such antibody may be used in therapy.

Therefore, in another aspect, the present invention provides for an antibody, preferably a monoclonal antibody, or a pharmaceutical composition comprising the antibody, and one or more pharmaceutically acceptable excipients, wherein the antibody comprises a first antigen-binding portion binding CD7 and a second antigen-binding portion binding CD9, wherein the antibody is preferably humanised and is for use in therapy.

In one embodiment, the antibody or composition comprising such antibody for use in therapy is an antibody comprising a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another aspect, the present invention provides for an antibody, preferably a monoclonal antibody, or a pharmaceutical composition comprising the antibody, and one or more pharmaceutically acceptable excipients, wherein the antibody comprises a first antigen-binding portion binding CD7 and a second antigen-binding portion binding CD9, wherein the antibody is preferably humanised and is for use in the treatment of cancer and/or an infectious disease.

In another embodiment, the antibody or composition comprising such antibody for use in the treatment of cancer and/or an infectious disease is an antibody comprising a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

An anti-CD7-CD9 antibody according to the present invention has shown that when both CD7 and CD9 are targeted through a bispecific antibody, the bispecific antibody is capable of promoting NK cells activity in the tumour microenvironment.

Hence, in another embodiment, the present invention provides for an antibody, preferably a monoclonal antibody, or a pharmaceutical composition comprising the antibody, and one or more pharmaceutically acceptable excipients, wherein the antibody comprises a first antigen-binding portion binding CD7 and a second antigen-binding portion binding CD9, wherein the antibody is preferably humanised and is for use in the treatment of cancer and/or an infectious disease, wherein the antibody is capable of promoting NK cells activity. Preferably, the antibody comprises a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In yet another aspect, the present invention provides for a method for treating a subject afflicted with cancer and/or an infectious disease, comprising administering to the subject a pharmaceutically effective amount of an antibody, preferably a monoclonal antibody, or a pharmaceutical composition comprising the antibody, and one or more pharmaceutically acceptable excipients, wherein the antibody comprises a first antigen-binding portion binding CD7 and a second antigen-binding portion binding CD9, wherein the antibody is preferably humanised.

The subjects to be treated is preferably a human subject. In one embodiment, there is provided for a method for treating a human subject afflicted with cancer and/or an infectious disease, comprising administering to the subject a pharmaceutically effective amount of an antibody, preferably a monoclonal antibody, or a pharmaceutical composition comprising the antibody and one or more pharmaceutically acceptable excipients, wherein the antibody comprises a first antigen-binding portion binding CD7 and a second antigen-binding portion binding CD9, wherein the antibody is preferably humanised.

In yet another embodiment, the method for treating a human subject afflicted with cancer and/or an infectious disease comprises administering to the human subject an antibody or composition comprising such antibody comprising a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another embodiment, there is provided for a method for treating a human subject afflicted with cancer and/or an infectious disease comprises administering to the human subject an antibody or composition comprising such antibody and one or more pharmaceutically acceptable excipients, wherein the antibody comprises a first antigen-binding portion binding CD7 and a second antigen-binding portion binding CD9, wherein the antibody is preferably humanised and wherein the antibody is capable of promoting NK cells activity. Preferably, the antibody comprises a first antigen-binding portion binding CD7 and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another embodiment, the first antigen-binding portion binding CD7 of the antibody of the present invention comprises a first heavy chain variable region and a first light chain variable region and the second antigen-binding portion binding CD9 comprises a second heavy chain variable region and a second light chain variable region and wherein:

a. The first heavy chain variable region comprises a CDR-H1 comprising SEQ ID NO: 3, a CDR-H2 comprising SEQ ID NO: 4 and a CDR-H3 comprising SEQ ID NO: 5; and b. The first light chain variable region comprises a CDR-L1 comprising SEQ ID NO: 6, a CDR-L2 comprising SEQ ID NO: 7 and a CDR-L3 comprising SEQ ID NO: 8; and c. The second heavy chain variable region comprises a CDR-H1 comprising SEQ ID NO: 9, a CDR-H2 comprising SEQ ID NO: 10 and a CDR-H3 comprising SEQ ID NO: 11; and d. The second light chain variable region comprises a CDR-L1 comprising SEQ ID NO: 12, a CDR-L2 comprising SEQ ID NO: 13 and a CDR-L3 comprising SEQ ID NO: 14;

or e. The first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21;

or f. The first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

In one embodiment, the antibody according to the present invention is prepared according to the disclosure of WO2015/181282, WO2016/009030, WO2016/009029, WO2017/093402, WO2017/093404 and WO2017/093406, which are all incorporated herein by reference.

More specifically, the antibody is made by the heterodimerization of a Fab-X and a Fab-Y.

Fab-X comprises a Fab fragment which comprises the first antigen-binding portion binding CD7 which comprises a first heavy chain variable region and a first light chain variable region wherein the first heavy chain variable region comprises a CDR-H1 comprising SEQ ID NO: 3, a CDR-H2 comprising SEQ ID NO: 4 and a CDR-H3 comprising SEQ ID NO: 5; and the first light chain variable region comprises a CDR-L1 comprising SEQ ID NO: 6, a CDR-L2 comprising SEQ ID NO: 7 and a CDR-L3 comprising SEQ ID NO: 8. The Fab comprising the first antigen-binding portion binding CD7 is linked to a scFv (clone 52SR4), preferably via a peptide linker to the C-terminal of the CH1 domain of the Fab fragment and the VL domain of the scFv. The scFv may itself also contains a peptide linker located in between its VL and VH domains.

Fab-Y also comprises a Fab fragment which comprises the second antigen-binding portion binding CD9 which comprises a second heavy chain variable region and a second light chain variable region and wherein the second heavy chain variable region comprises a CDR-H1 comprising SEQ ID NO: 9, a CDR-H2 comprising SEQ ID NO: 10 and a CDR-H3 comprising SEQ ID NO: 11; and the second light chain variable region comprises a CDR-L1 comprising SEQ ID NO: 12, a CDR-L2 comprising SEQ ID NO: 13 and a CDR-L3 comprising SEQ ID NO: 14. The Fab comprising the second antigen-binding portion binding CD9 is linked to a peptide GCN4 (clone 7P14P), preferably via a peptide linker to the CH1 domain of the Fab fragment.

The scFv of Fab-X is specific for and complementary to the peptide GCN4 of Fab-Y. As a result, when the Fab-X and the Fab-Y are brought into contact with each other, a non-covalent binding interaction between the scFv and GCN4 peptide occurs, thereby physically retaining the two antigen-binding portions in the form of a complex resulting in an antibody comprising two antigen-binding portions on the same molecule (FIG. 1).

In another embodiment, the Fab-X comprises the first antigen-binding portion binding CD7 which comprises a first heavy chain variable region comprising SEQ ID NO: 15 and the first light chain variable region comprising SEQ ID NO: 17; and Fab-Y comprises the second antigen-binding portion binding CD9 which comprises the second heavy chain variable region comprising SEQ ID NO: 19 and second light chain variable region comprising SEQ ID NO: 21.

Binding specificities may be exchanged between Fab-X and Fab-Y, i.e. in one embodiment Fab-X may comprise the antigen-binding portion binding to CD7 and Fab-Y the antigen-binding portion binding to CD9, in another embodiment, Fab-Y may comprise the antigen-binding portion binding to CD7 and Fab-X the antigen-binding portion binding to CD9.

In another aspect of the present invention, there is provided the use of an antibody, preferably a monoclonal antibody, or a pharmaceutical composition comprising the antibody, and one or more pharmaceutically acceptable excipients, wherein the antibody comprises a first antigen-binding portion binding CD7 and a second antigen-binding portion binding CD9, wherein the antibody is preferably humanised, in the manufacture of a medicament for treating cancer and/or an infectious disease.

Example of cancers that may be treated using the antibody, or pharmaceutical composition comprising such antibody, include but are not limited to, liver cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the oesophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukaemia, chronic lymphoid leukaemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukaemia, mycosis fungoides, anaplastic large cell lymphoma, T-cell lymphoma, and precursor T-lymphoblastic lymphoma, and any combinations of said cancers. The present invention is also applicable to treatment of metastatic cancers.

The antibody according to the present invention, or the pharmaceutical composition comprising such antibody, may be administered concomitantly or sequentially to one or more additional cancer therapies. By cancer therapies is intended drug-based therapies as well as other type of cancer therapies such as radiotherapies.

The invention will now be further described by way of examples with references to embodiments illustrated in the accompanying drawings.

EXAMPLES

Example 1: T Cell Activation Primary Screen

The activation status of T cells can be assessed through their expression of cell surface markers and secreted cytokines which play important roles in cellular function. Activated T cells produce increased amounts of granzyme B, IFNgamma and IL-2, essential mediators to effect killing of virus-infected or tumour cell targets. T cells in the tumour microenvironment are often maintained in a suppressed state and express only low levels of these proteins. Agents that overcome this suppression and induce T cell activation, proliferation and cytotoxic activity have tremendous therapeutic potential as they may unleash effective anti-tumour T cell responses and promote cancer elimination.

To identify novel modulators of T cell activation, a large screen was undertaken whereby 49 antigen specificities were combined to generate a grid of bispecific antibodies with a theoretical size of 1,176 possible bispecific combinations. The specificities were selected from the literature as being expressed on T cells or expressed on other cell types involved in interactions with T cells. Of this potential grid, 969 novel antigen bispecific constructs were tested, covering 82.4% of the possible combinations. Between 1 and 4 different antibodies were tested for each specificity, and all were tested on peripheral blood mononuclear cells (PBMC) from donors in combination with a negative control arm to identify the effect of the monovalent forms of the construct.

PBMC represent the major leukocyte classes involved in both innate and adaptive immunity, apart from granulocytes. PBMC comprise a heterogenous population of cells which when manipulated in vitro provide a relatively more relevant physiological environment compared to isolated component cell types such as T cells and monocytes, that are no longer capable of responding to paracrine and autocrine signals provided by other cells. As such identification of molecules modulating specific subsets of cells within the wider PBMC population, have increased translational potential to more complex biological systems, ultimately increasing success rates for modulating immune cell interactions in disease.

Each bispecific combination was tested on two PBMC donors. This negative control arm is a Fab from an antibody raised to an antigen not expressed on PBMC.

Fusion proteins were prepared according to the disclosure of WO2015/181282, WO2016/009030, WO2016/009029, WO2017/093402, WO2017/093404 and WO2017/093406, which are all incorporated herein by reference. The first fusion protein (A-X) includes a Fab fragment (A of the A-X) with specificity to one antigen, which is linked to X, a scFv (clone 52SR4) via a peptide linker to the C-terminal of the CH1 domain of the Fab fragment and the VL domain of the scFv. The scFv itself also contains a peptide linker located in between its VL and VH domains.

The second fusion protein (B-Y) includes a Fab fragment (B of the B-Y) with specificity to another antigen. However, in comparison to the first protein, the Fab fragment B is attached to Y, a peptide GCN4 (clone 7P14P) via a peptide linker to the CH1 domain of the Fab fragment.

The scFv, X, is specific for and complementary to the peptide GCN4, Y. As a result, when the two fusion proteins are brought into contact with each other, a non-covalent binding interaction between the scFv and GCN4 peptide occurs, thereby physically retaining the two fusion proteins in the form of a complex mimicking an antibody comprising antigen-binding portion on the same molecule (FIG. 1).

Figure 2:
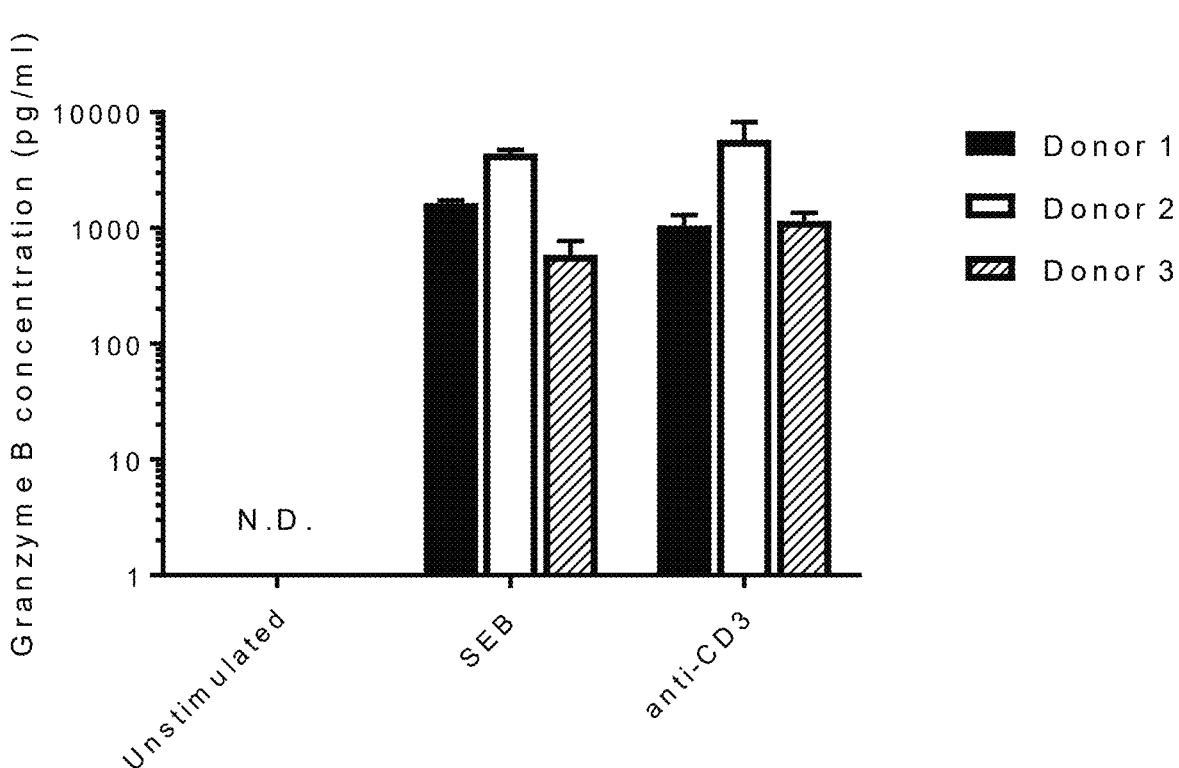
FIG. 2. Concentrations of granzyme B using an Intelli-Cyt® QBead PlexScreen for unstimulated and anti-CD3 or Super antigen (SAg) *Staphylococcus aureus* Enterotoxin B (SEB) stimulated control samples. N.D.=None detected (level of detection (LOD)=40 pg/mL). Peripheral blood mononuclear cell (PBMC) cultures were treated with SEB at 1 µg/mL or anti-CD3 (UCHT1) at 250 ng/mL or unstimulated for 48 hours. The conditioned medium was collected and diluted 40-fold before analysis of the level of granzyme B.
Figure 3:
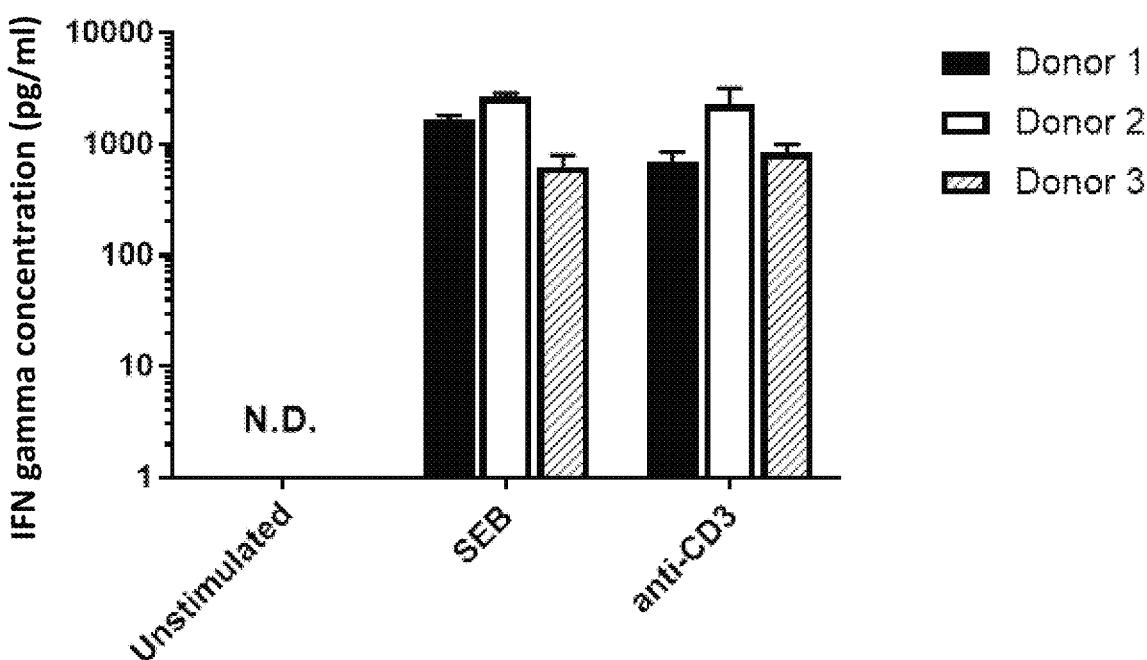
FIG. 3. Concentration of Interferon gamma (IFNgamma) using an IntelliCyt® QBead PlexScreen for unstimulated and anti-CD3 (UCHT1) or SAg SEB stimulated control samples. N.D.=None detected (LOD=10 pg/mL). PBMC cultures were treated with SEB at 1 µg/mL or anti-CD3 (UCHT1) at 250 ng/mL or unstimulated for 48 hours. The conditioned medium was collected and diluted 40-fold before analysis of the level of IFNgamma.

Purified Fab-X and Fab-Y with varying specificities were incubated together for 60 minutes (in a 37° C./5% $CO_2$ environment) at an equimolar concentration. The final molarity of each tested complex was 100 nM. In 384-well tissue culture plates, $1\times10^5$ PBMC were added to wells, to which were added pre-formed Fab-X/Fab-Y bispecific antibodies. Following the bispecific antibodies addition, the cells were incubated for 48 hours at 37° C./5% $CO_2$, with or without 1 μg/mL (final concentration) Staphylococcal Enterotoxin-B superantigen (SEB) or 250 ng/mL (final concentration) anti-human CD3 antibody (clone UCHT1). After 48 hours the plates were centrifuged at 500×g for 5 minutes at 4° C. Cell culture supernatant was transferred from the cell pellets to fresh plates and frozen at −80° C. The levels of granzyme B or interferon gamma (IFNgamma) in unstimulated or anti-CD3 or SEB stimulated conditions were then studied. The conditioned media from the untreated samples were thawed and diluted 40-fold before analysis of the level of Granzyme B (FIG. 2) or IFNgamma (FIG. 3), measured to create untreated baselines. The PBMC culture conditioned media treated with the antibodies were thawed and diluted 20-fold for the anti-CD3 and SEB stimulated plates, and 5-fold for the unstimulated plates. The diluted conditioned medium was then assayed for levels of the proteins granzyme B and IFNgamma using an IntelliCyt® QBead PlexScreen.

When considering antigen pairs capable of upregulating the levels of Granzyme B and IFNgamma in the supernatant in conjunction with SEB and anti-CD3, CD7-CD9 combinations were identified. The CD7-CD9 combination was therefore taken into subsequent assays to show that it is repeatable across an increased number of donors.

Example 2: CD7-CD9 Follow Up Assay

To confirm the effect of an anti-CD7/CD9 antibody on stimulation of T cells, a further 3 PBMC donors were assayed in SEB and anti-CD3 stimulated and unstimulated conditions.

A grid of fusion proteins Fab-X and Fab-Y were created by diluting equimolar (1 μM) quantities of Fab-X (Fab-scFv) and Fab-Y (Fab-peptide) with specificity for CD7 and CD9 in TexMACS™ media (Miltenyi Biotec®) containing 100 U/mL penicillin/100 μg/mL streptomycin. Mixtures of equimolar (1 μM) Fab-Y proteins were also generated in the same manner. The Fab-X and Fab-Y fusion proteins were incubated together for 1 hour (in a 37° C./5% $CO_2$ environment), at a final concentration of 500 nM. Negative control wells contained TexMACS™ media only were also generated alongside the Fab-X and Fab-Y wells.

During this time, cryopreserved human PBMC isolated from platelet leukapheresis cones were thawed and washed in TexMACS™ media and resuspended at $3.33×10^6$ cells/mL. The PBMC were then seeded into 384-well flat bottom tissue culture plates (Greiner Bio-One®) at 30 μL/well ($1×10^5$ PBMC). A total of 10 μl of Fab-X/Fab-Y bispecific antibodies were transferred to the plates containing 30 μL PBMC. The PBMC were then either left unstimulated by the addition of 10 μL of TexMACS™ media, or stimulated with 10 μL of either soluble anti-CD3 (UCHT1) (250 or 10 ng/mL final concentration) or SEB (1 μg/mL final concentration). This resulted in a final assay concentration of Fab-X/Fab-Y bispecific antibodies of 100 nM. The plates were then returned to a 37° C./5% $CO_2$ environment for 48 hours.

After 48 hours the plates were centrifuged at 500×g for 5 minutes at 4° C. Conditioned medium was transferred from the cell pellets to fresh plates and frozen at −80° C. On the day of analysis, the conditioned medium was thawed and diluted 40-fold in RPMI cell culture medium (ThermoFisher). The diluted conditioned medium was then assayed for levels of granzyme B and IFNgamma using an IntelliCyt® QBead PlexScreen. Standards curves of known protein concentrations were generated alongside, allowing for the calculation of the absolute concentrations for these proteins in the conditioned medium.

The data analysis software package ForeCyt™ (IntelliCyt®) was used to measure the median fluorescent intensity values for the granzyme B and IFNgamma detection beads. The data were then used to generate standard curves and calculate the concentrations. The log 2 fold changes of granzyme B and IFNgamma concentrations were calculated relative to control well values.

Figure 4:
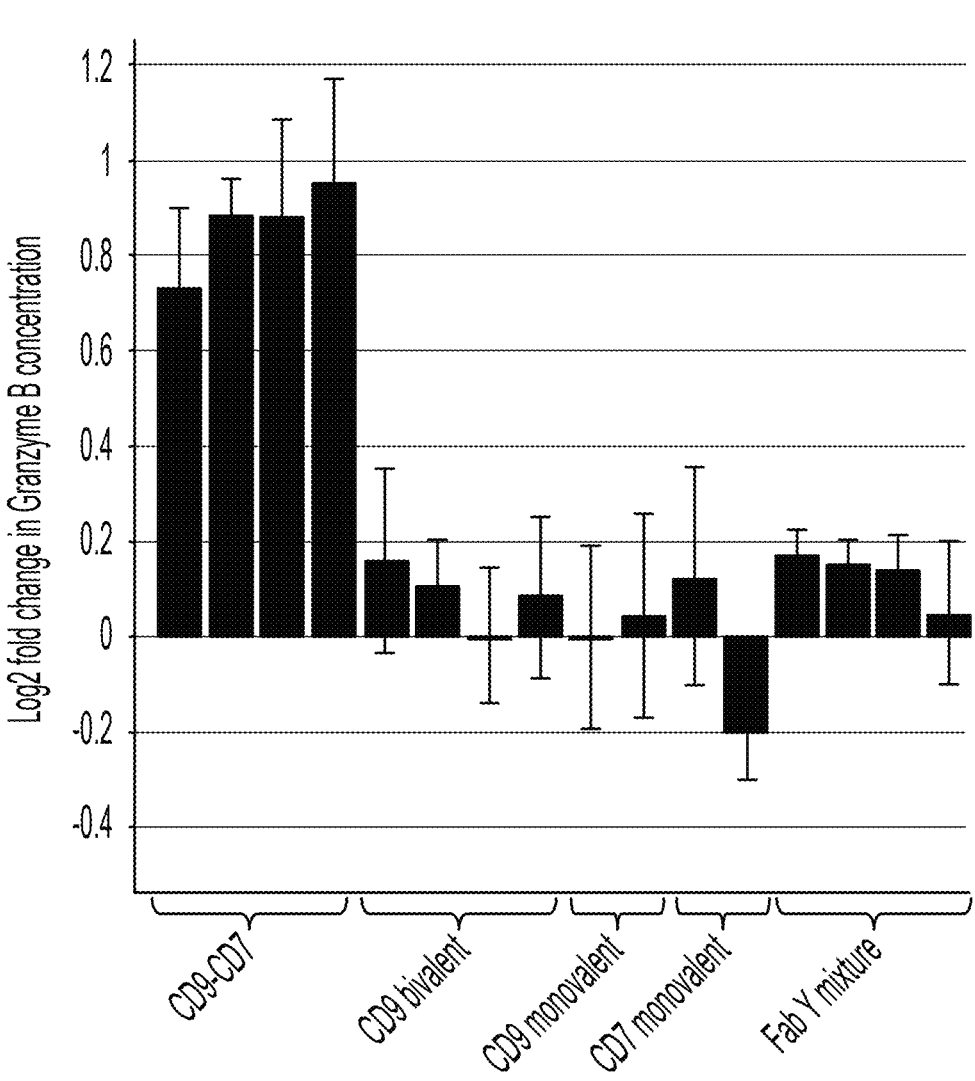
FIG. 4. $Log_2$ Fold Change in the concentration of granzyme B levels using an IntelliCyt® QBead PlexScreen in the supernatant of PBMC cultures in the presence of SEB (1 µg/mL) stimulation. $Log_2$ fold changes were calculated for the concentrations of granzyme B levels in the samples treated with the antibodies relative to the SEB stimulated controls. N=3 donors, 2 technical replicates±standard error of the mean (SEM). PBMC cultures were treated with SEB at 1 µg/mL for 48 hours in the presence of either the CD7-CD9 bispecific antibodies or control antibodies. The conditioned medium was collected and diluted 40-fold before analysis of the level of granzyme B.
Figure 6:
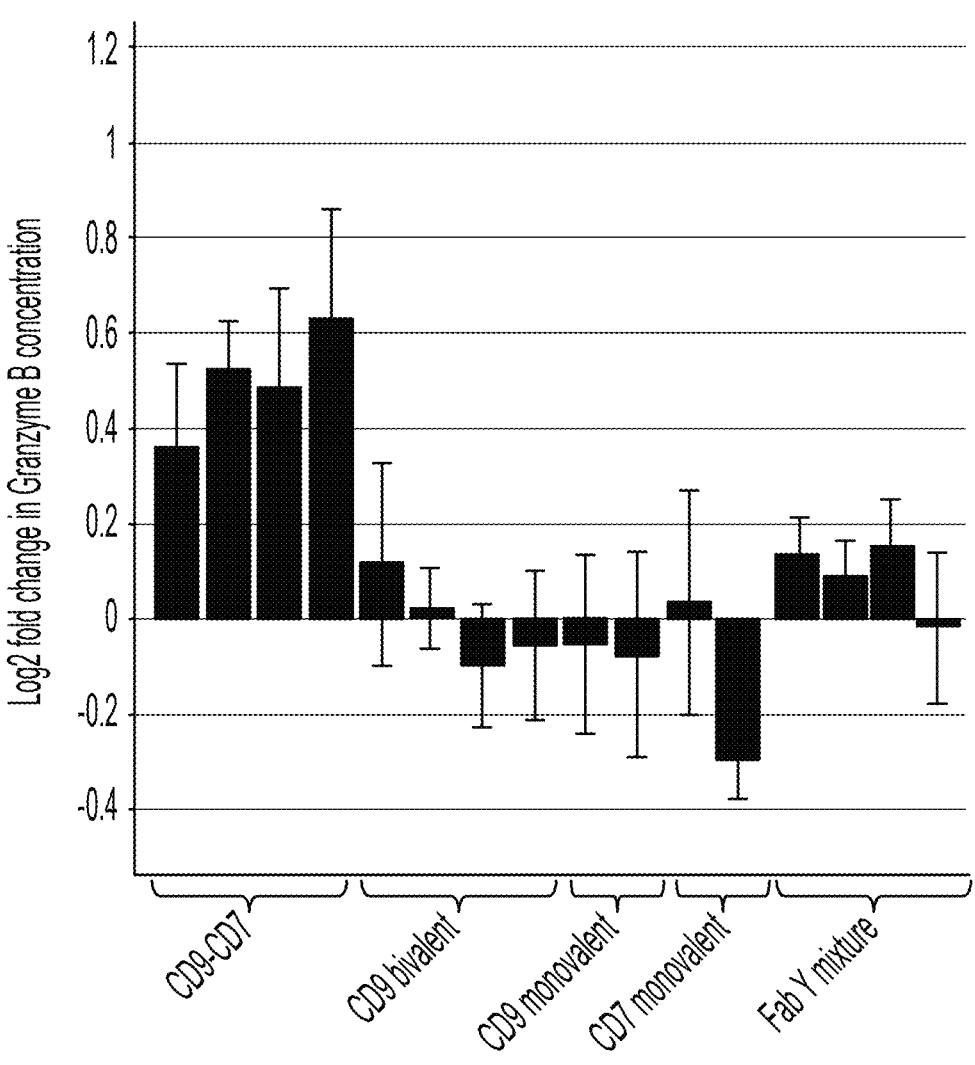
FIG. 6. Log 2 Fold Change in the concentration of granzyme B levels using an IntelliCyt® QBead PlexScreen in the supernatant of PBMC cultures in the presence of anti-CD3 (UCHT1) stimulation. $Log_2$ fold changes were calculated for the concentrations of granzyme B levels in the samples treated with the antibodies relative to the SEB stimulated controls. N=3 donors, 2 technical replicates ±SEM. PBMC cultures were treated with anti-CD3 at 250 ng/mL for 48 hours in the presence of either the CD7-CD9 bispecific antibodies or control antibodies. The conditioned medium was collected and diluted 40-fold before analysis of the level of Granzyme B.

Four CD7/CD9 bispecific antibodies showed increased levels of secreted granzyme B under SEB (FIG. 4) and anti-CD3 stimulation (FIG. 6). The control constructs did not lead to this increase; the CD9 bivalents (i.e. formed by a fusion where both Fab in the Fab-X and Fab-Y are specific for CD9) and monovalent antibodies for CD9 or CD7 (i.e. formed by a fusion where the Fab is specific for CD9 or CD7 but the other component Fab is a negative control) did not lead to a similar increase in the secretion of granzyme B, suggesting that the binding of either CD9 or CD7 alone cannot induce granzyme B secretion in the absence of the other.

Figure 5:
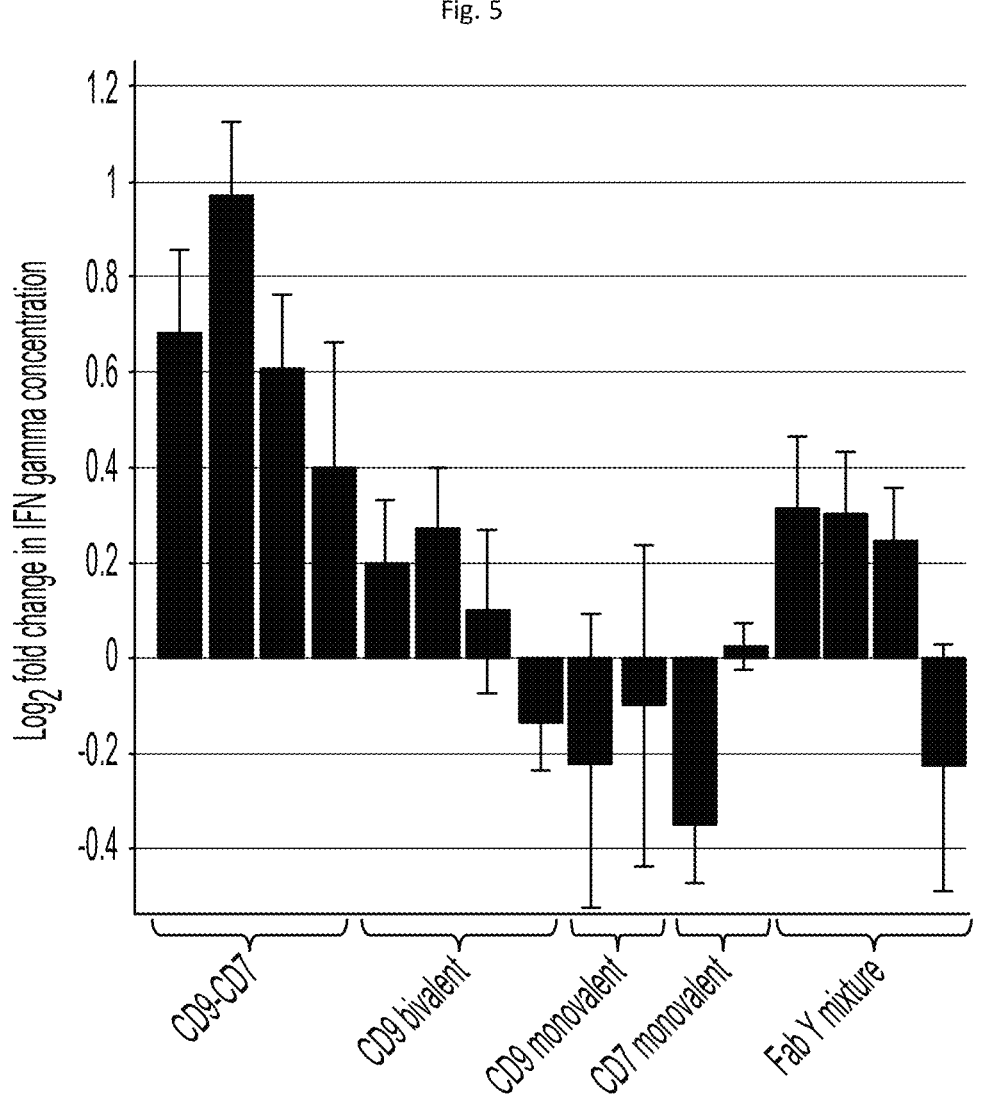
FIG. 5. $Log_2$ Fold Change in the concentration of IFNgamma levels using an IntelliCyt® QBead PlexScreen in the supernatant of PBMC cultures in the presence of SEB (1 µg/mL) stimulation. $Log_2$ fold changes were calculated for the concentrations of IFNgamma levels in the samples treated with the antibodies relative to the SEB stimulated controls. N=3 donors, 2 technical replicates ±SEM. PBMC cultures were treated with SEB at 1 µg/mL for 48 hours in the presence of either the CD7-CD9 bispecific antibodies or control antibodies. The conditioned medium were collected and diluted 40-fold before analysis of the level of IFNgamma.
Figure 7:
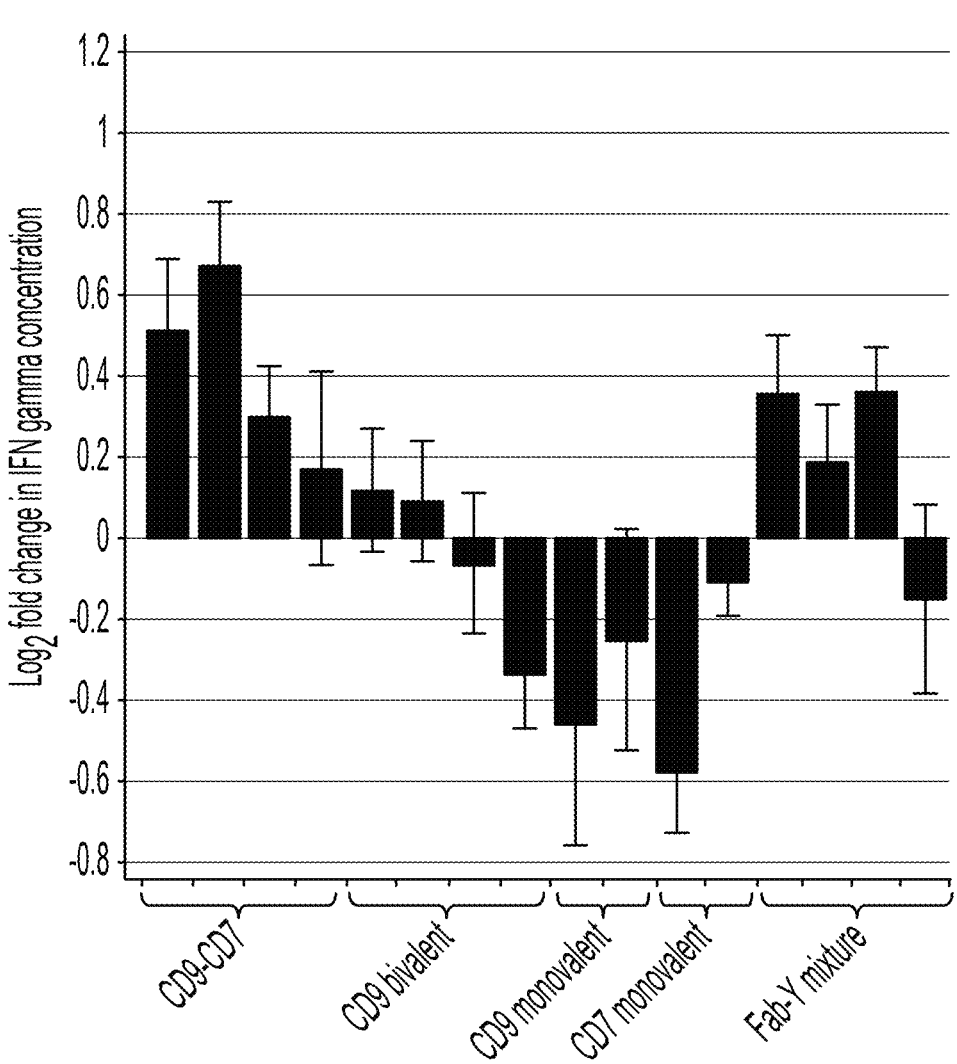
FIG. 7. Log 2 Fold Change in the concentration of IFNgamma levels using an IntelliCyt® QBead PlexScreen in the supernatant of PBMC cultures in the presence of anti-CD3 (UCHT1) stimulation. $Log_2$ fold changes were calculated for the concentrations of IFNgamma levels in the treated samples relative to the SEB stimulated controls. N=3 donors, 2 technical replicates ±SEM. PBMC cultures were treated with anti-CD3 (clone UCHT1) at 250 ng/mL for 48 hours in the presence of either the CD7-CD9 bispecific antibodies or control antibodies. The conditioned medium was collected and diluted 40-fold before analysis of the level of IFNgamma.

Similar increases in IFNgamma could be detected for the CD9-CD7 bispecific antibodies, although to a lesser degree that that seen for granzyme B (FIGS. 5, for SEB stimulation and FIG. 7 for the anti-CD3 stimulation). The response of the CD9 bivalent antibodies and monovalent controls was less clear also with a range of small increases and decreases in the level of secreted IFNgamma in either anti-CD3 or SEB stimulated conditions. However, there remained a clear enhancement of response, particularly in SEB stimulated conditions, of the CD7-CD9 bispecific antibodies as opposed to anti-CD7 and anti-CD9 antibodies as a mixture.

Example 3: Effect of a CD7-CD9 Bispecific Antibody on T Cell Proliferation

The effect of an anti-CD7/CD9 antibody on proliferation of CD4+ and CD8+ T cells was assessed in 5 PBMC donors. Mixtures of fusion proteins Fab-X and Fab-Y were created by diluting equimolar (1 μM) quantities of Fab-X (Fab-scFv) and Fab-Y (Fab-peptide) with specificity for CD7 and CD9 in DMEM (ThermoFisher) containing 10% FBS and 100 U/mL penicillin/100 μg/mL streptomycin. Mixtures of equimolar (1 μM) Fab-Y proteins were also generated in the same manner. The Fab-X and Fab-Y fusion proteins were incubated together for 1 hour (in a 37° C./5% $CO_2$ environment).

During this time, cryopreserved human PBMC isolated from platelet leukapheresis cones were thawed, washed in DMEM media and resuspended at approximately $2×10^6$ cells/mL in PBS. Cell Trace™ Violet (CTV; ThermoFisher) was then added to a final concentration of 1 μM (2 μL 5 mM CTV in DMSO added to 10 mL cells), incubated in the dark at room temperature for 20 minutes, the cells washed twice with DMEM and resuspended in media to a final concentration of $1×10^6$ cells/mL.

Fab-X/Fab-Y bispecific antibodies were diluted to 400 nM concentration in DMEM and 50 μL transferred in triplicate to wells of a 96-well U bottom tissue culture plate. Anti-CD3 (UCHT1), 50 μL of a 200 ng/mL solution in DMEM, was then added. To 3 wells 100 μL DMEM media alone was added as a negative proliferation control. Finally, 100 μL of CTV labelled PBMC were added to each well. This resulted in a final assay concentration of Fab-X/Fab-Y bispecific antibodies of 100 nM, 50 ng/mL anti-CD3 and $1×10^5$ cells/well. The plates were then returned to a 37° C./5% $CO_2$ environment for 96 hours.

After 96 hours the plates were centrifuged at 300×g for 5 minutes. Conditioned medium was removed, the cells were washed twice with FACS buffer (PBS/2% FBS) and then resuspended in 50 µL FACS buffer containing fluorescently labelled antibodies, as listed in Table 2. The cells were incubated at room temperature in the dark for 20 min, washed twice with FACS buffer, resuspended in 100 µL/per well FACS buffer and analysed by flow cytometry (BD FACS Canto II™). Total events from 50 µL (50% volume) of each well were collected.

The data analysis software package FlowJo® was used to gate on CD8+ and CD4+ cells. Cell proliferation was assessed by enumerating cells with reduced CTV staining relative to unstimulated cells. The data are presented as the mean±SEM for triplicate wells.

TABLE 2

| Epitope | Fluorophore | Clone | Source | Dilution |
|---------|-------------|-------|--------|----------|
| CD8 | PE | RPA-T8 | BD | 100 |
| CD4 | APC | RPA-T4 | BioLegend ® | 20 |

Figure 8:
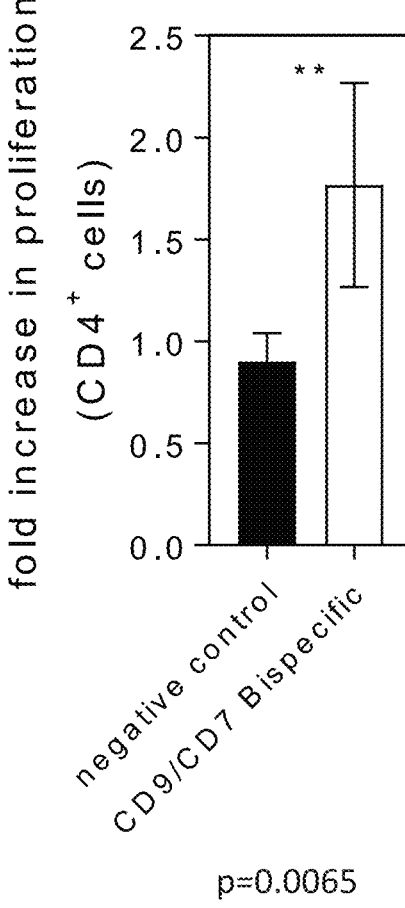
FIG. 8. Numbers of proliferating CD8+ and CD4+ T cells in the presence of anti-CD3 (clone UCHT1) (50 ng/mL) stimulation. Human PBMC were labelled with Cell Trace™ Violet (CTV) then incubated in triplicate wells for 4 days with anti-CD3 (clone UCHT1) plus 100 nM of the CD7-CD9 bispecific antibodies. T cell proliferation was assessed by flow cytometry by gating on CD8+ and CD4+ populations and enumeration of CTV low cells. Results are presented as the mean±SEM of 5 PBMC donors. Statistically significant differences are highlighted with p values <0.01 (Mann-Whitney test).
Figure 8:
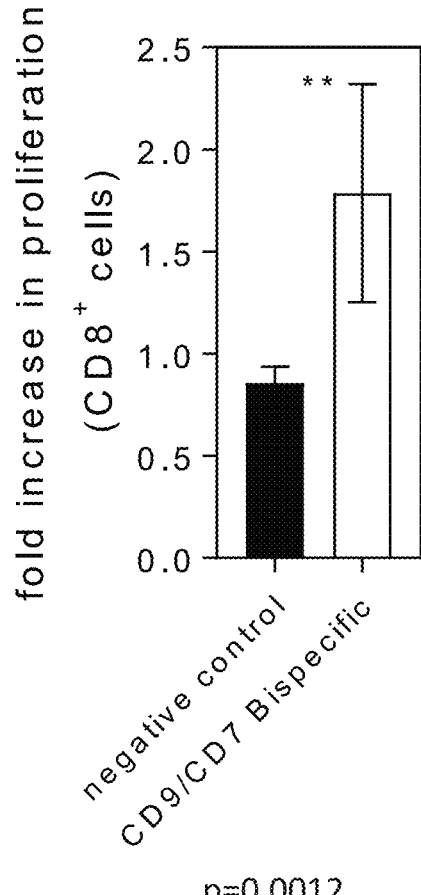

As shown in FIG. 8, proliferation of CD8+ and CD4+ T cells in the presence of anti-CD3 (50 ng/mL) stimulation was statistically significantly higher when human PBMC were treated with the CD7/CD9 bispecific antibody versus the negative control (no bispecific antibody). The significance of this difference between treatment with control and bispecific antibody is expressed as a p value calculated using Mann-Whitney test.

Example 4: Effect of a CD7-CD9 Bispecific Antibody on NK Cell Activation and Degranulation Natural killer (NK) cells are a subset of lymphocytes that play a central role in the innate immune response to tumours and viral infections. They kill by a mechanism termed "degranulation" that involves the release of cytolytic granules containing granzyme B and perforin. NK cells are key effectors in cancer immunosurveillance and have many different mechanisms to distinguish targets cells from healthy cells based on complex balance in expression of activating and inhibitory receptors. The tumour microenvironment exploits these mechanisms to inhibit NK activity and different strategies are being explored to try and enhance their activity and/or prevent their suppression by the tumour microenvironment for cancer immunotherapy (Guillery, C. et al. Nat. Immunol. 17 (9) 1025-1036. 2016).

During degranulation, cytolytic granules in NK cells are released and the lysosome-associated membrane protein-1 (LAMP-1, CD107a) which is present on cytolytic granules surface is transported to the cell surface and becomes measurable as a biomarker of NK cell degranulation activity. This results in the expression of lysosomal proteins such as CD107a on the cell surface which can be used as a sensitive marker of cytotoxic degranulation.

The effect of an anti-CD7/CD9 bispecific antibody on NK cell activation and degranulation was assessed in 3 PBMC donors. Mixtures of fusion proteins Fab-X and Fab-Y were created by diluting equimolar (400 nM) quantities of Fab-X (Fab-scFv) and Fab-Y (Fab-peptide) with specificity for CD7 and/or CD9 in RPMI (ThermoFisher) containing 10% FBS and 2 mM GlutaMAX. Mixtures of equimolar (400 nM) Fab-Y proteins were also generated in the same manner. The Fab-X and Fab-Y fusion proteins were incubated together for 1 hour in a 37° C./5% CO$_2$ incubator. Following this incubation 50 µL of each antibody was transferred in quadruplicate to wells of a 96 well U bottom tissue culture plate.

During this time, PBMC were isolated from fresh whole blood using centrifugation and were washed twice in PBS. The cells were resuspended at 5×10$^6$ cells/mL in RPMI media and 100 µL was transferred into the assay plate containing the antibodies. The plate was placed in a 37° C./5% CO$_2$ incubator for 30 minutes.

After 30 minutes K562 target cells were resuspended at 1×10$^6$ cells/mL in RPMI and 50 µL was added to the plate containing PBMC and antibodies. This equates to an effector to target ratio (E:T) of 10:1. The final assay concentration of Fab-X+Fab-Y complexes equates to 100 nM. The assay plate was then returned to the 37° C./5% CO$_2$ incubator for 2 hours. PBMC cultured alone, with no target cells, were used as a negative control for degranulation.

After 2 hours the plate was centrifuged at 300×g for 3 minutes. Conditioned medium was removed, the cells were washed twice with cell staining buffer (Biolegend) and then resuspended in 100 µL cell staining buffer containing fluorescently labelled antibodies, as listed below in Table 3. The cells were incubated at 4° C. in the dark for 20 minutes, washed twice with cell staining buffer, resuspended in 150 µL/per well PBS and analysed by flow cytometry (BD FACS Canto II™). From each well 100 µL of each sample was collected.

The data analysis software package FlowJo® was used to gate on CD3-CD56+NK cells. Degranulation and activation of NK cells was assessed by analysing appearance of cell surface CD107a or CD69 geometric mean fluorescence. The percentage increase in CD107a+ cells or percentage increase in CD69 was calculated compared to levels observed in PBMC and K562 co-cultures without any antibodies. The data from the three donors was pooled and presented as both individual donors (black circles) and the mean±SEM (horizontal line).

TABLE 3

| Epitope | Fluorophore | Clone | Source | Dilution |
|---------|-------------|-------|--------|----------|
| CD3 | FITC | UCHT1 | Biolegend | 100 |
| CD56 | Brilliant Violet 421 ™ | HCD56 | Biolegend | 100 |
| CD107a | APC | H4A3 | Biolegend | 100 |
| CD69 | PerCP | FN50 | Biolegend | 100 |

Figure 9:
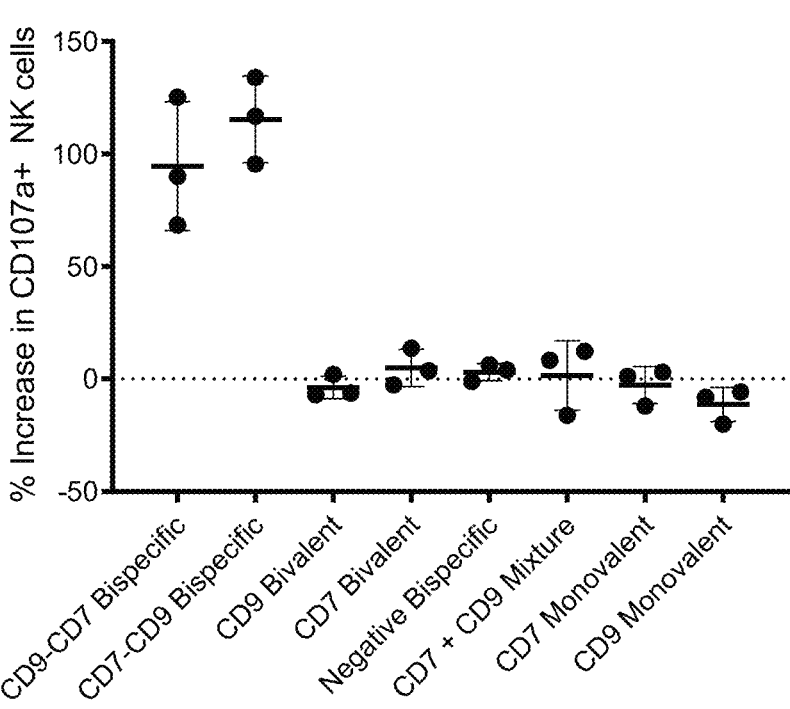
FIG. 9. NK cell activation and degranulation following co-culture with K562 target cells. Human PBMC cells were co-cultured with K562 target cells at an effector to target ratio (E:T) ratio of 10:1 in the presence of 100 nM of the CD7-CD9 bispecific antibodies and control antibodies for 2 hours at 37° C., 5% $CO_2$. Each condition was tested in quadruplicate wells. NK cell degranulation was measured by flow cytometry by gating on CD3-CD56+CD107a+ cells. NK cell activation was measured by gating on CD3-CD56+ CD69+ cells. Results from 3 donors were pooled and data is presented as individual donors (black circles) or mean±SEM (horizontal line).
Figure 9:
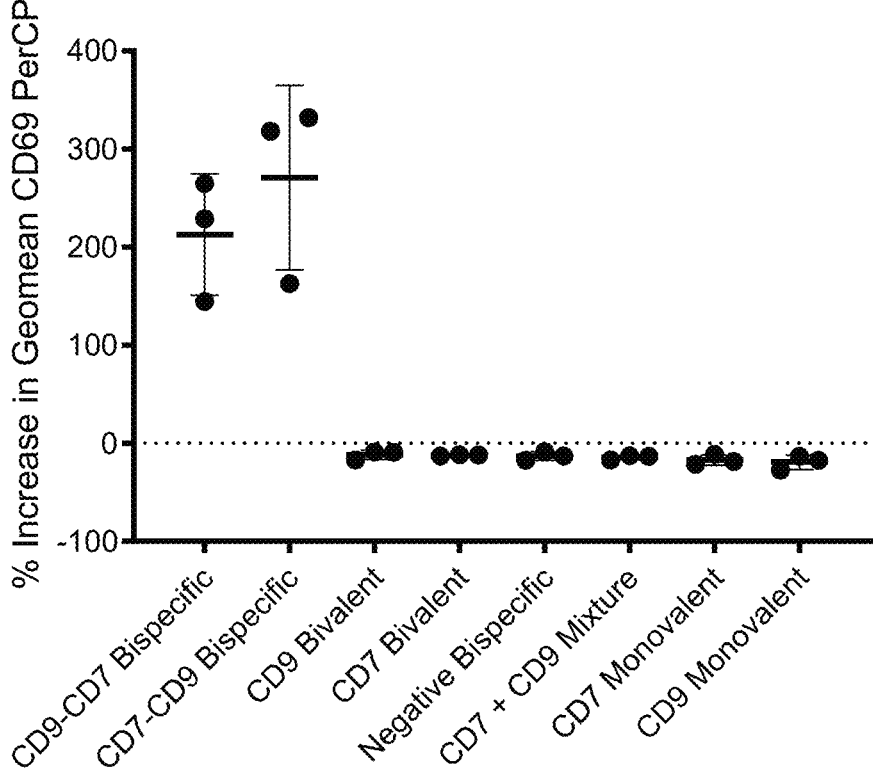

As shown in FIG. 9 degranulation of NK cells is greatly increased following treatment with CD7-CD9 bispecific antibodies. The increase in CD107a+NK cells is only observed when the two antigens are targeted with the bispecific CD7-CD9, as bivalent and monovalent controls do not change the level of degranulation. This increase in degranulation following treatment with CD7-CD9 bispecific antibodies is matched by an increase in NK cells activation as shown by an increase in CD69 expression. These results suggest that an anti-CD7-CD9 bispecific antibody according to the present invention may promote NK cells activity in the tumour microenvironment for cancer immunotherapy.

Example 5: CD7-CD9 Variable Region Diversity

To better understand how the effect of CD7-CD9 bispecific is reproducible with different V region sequences, a further 3 PBMC donors were assayed in SEB stimulated conditions treated with CD7-CD9 Fab-K$_D$-Fab antibodies generated from 14 different CD7 variable regions and 7 different CD9 variable regions and the increase in granzyme B secretion measured.

These different variable regions (with a numerical identifier) were combined with each other and a negative control V region (5599) to generate bispecific, bivalent and monovalent combinations in a grid format as represented in Table 4.

MACS™ media or stimulated with 20 µL of SEB (1 µg/mL final concentration). This resulted in a final assay concentration of Fab-X and Fab-Y complexes of 100 nM. The plates were then returned to a 37° C., 5% $CO_2$ environment for 48 hours.

After 48 hours the plates were centrifuged at 500×g for 5 minutes at 4° C. Conditioned media were transferred from the cell pellets to fresh plates and frozen at −80° C. On the

TABLE 4

| | | | Fab-X | | | | | | | | | |
|---|---|---|---|---|---|---|---|---|---|---|---|---|
| | | | CD9 | | | | | | CD7 | | | |
| | | | 7270 | 7271 | 7272 | 7485 | 7486 | 7489 | 8850 | 8853 | 8860 | 8871 | 8878 |
| Fab-Y | CD9 | 7270 | | | Bivalent | | | | | Bispecific | | | |
| | | 7271 | | | | | | | | | | | |
| | | 7272 | | | | | | | | | | | |
| | | 7485 | | | | | | | | | | | |
| | | 7486 | | | | | | | | | | | |
| | | 7489 | | | | | | | | | | | |
| | | 7491 | | | | | | | | | | | |
| | CD7 | 8850 | | | Bispecific | | | | | Bivalent | | | |
| | | 8853 | | | | | | | | | | | |
| | | 8854 | | | | | | | | | | | |
| | | 8860 | | | | | | | | | | | |
| | | 8871 | | | | | | | | | | | |
| | | 8878 | | | | | | | | | | | |
| | | 8879 | | | | | | | | | | | |
| | | 8881 | | | | | | | | | | | |
| | Con | 5599 | | | | Monovalent | | | | | | | |

| | | | Fab-X | | | | | | | | Con |
|---|---|---|---|---|---|---|---|---|---|---|---|
| | | | CD7 | | | | | | | | |
| | | | 8879 | 8881 | 8849 | 8852 | 8855 | 8856 | 8876 | 8877 | 5599 |
| Fab-Y | CD9 | 7270 | | | | Bispecific | | | | | Monovalent |
| | | 7271 | | | | | | | | | |
| | | 7272 | | | | | | | | | |
| | | 7485 | | | | | | | | | |
| | | 7486 | | | | | | | | | |
| | | 7489 | | | | | | | | | |
| | | 7491 | | | | | | | | | |
| | CD7 | 8850 | | | | Bivalent | | | | | |
| | | 8853 | | | | | | | | | |
| | | 8854 | | | | | | | | | |
| | | 8860 | | | | | | | | | |
| | | 8871 | | | | | | | | | |
| | | 8878 | | | | | | | | | |
| | | 8879 | | | | | | | | | |
| | | 8881 | | | | | | | | | |
| | Con | 5599 | | | | Monovalent | | | | | |

A grid of fusion proteins Fab-X and Fab-Y were created by diluting equimolar (1 µM) quantities of Fab-X (Fab-scFv) and Fab-Y (Fab-peptide) with specificity for CD9 and CD7 in TexMACS™ media (Miltenyi Biotec®) containing 100 U/mL penicillin/100 µg/mL streptomycin. The Fab-X and Fab-Y fusion proteins were incubated together for 1 hour (in a 37° C., 5% $CO_2$ environment), at a final concentration of 500 nM. Negative control wells containing TexMACS™ media only were also generated alongside the Fab-X and Fab-Y wells.

During this time, cryopreserved human PBMCs isolated from platelet leukapheresis cones were thawed and washed in TexMACS™ media and resuspended at $2.5 \times 10^6$ cells/mL. The PBMCs were then seeded into 96-well U-bottom tissue culture plates (Costar) at 60 µL/well ($1.5 \times 10^5$ PBMC).

20 µL of Fab-X and Fab-Y complexes were transferred to the plates containing 60 µL PBMC. The PBMC were then either left unstimulated by the addition of 20 µL of Texday of analysis, the conditioned media were thawed and diluted 50-fold in RPMI and assayed for levels of granzyme B using an IntelliCyt® QBead® PlexScreen.

The data analysis software package ForeCyt™ (IntelliCyt®) was used to measure the median fluorescent intensity values for the granzyme B detection beads. The log 2 fold changes of granzyme B MFI were calculated relative to control well values.

Figure 10:
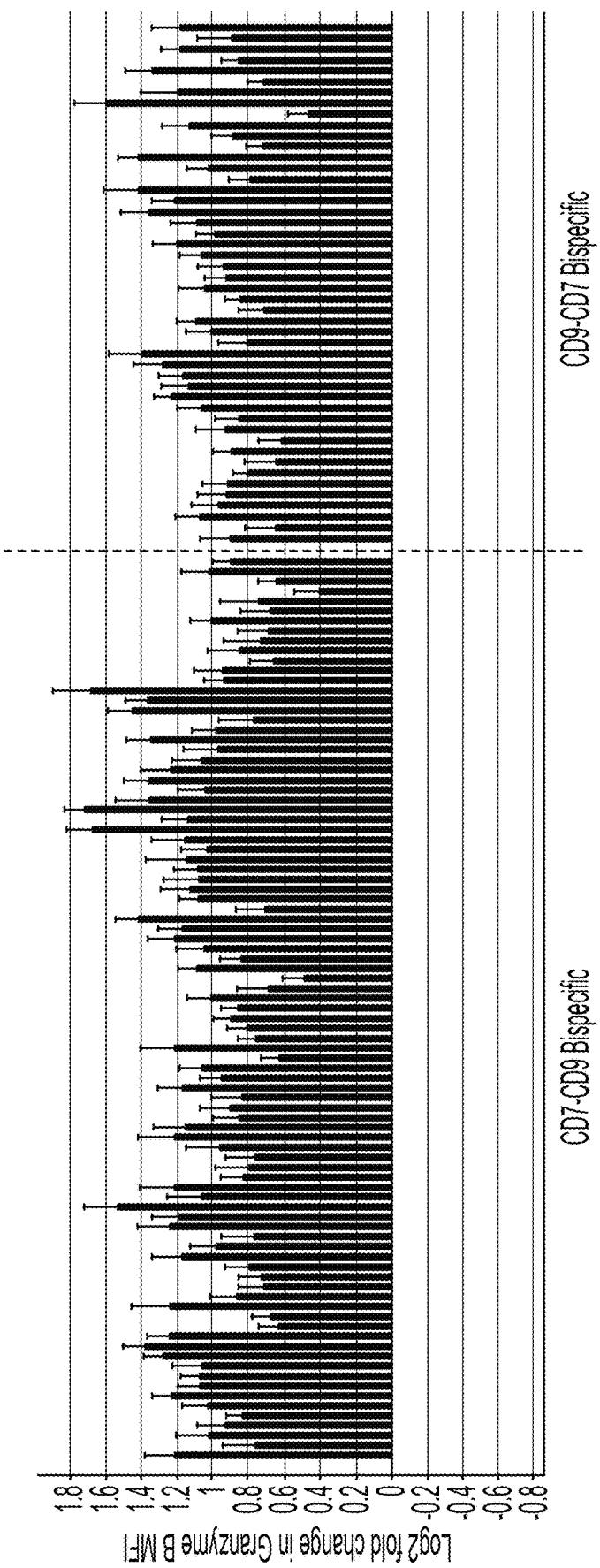
FIG. 10. Log 2 fold change in the MFI of granzyme B levels in the conditioned medium of PBMC cultures in the presence of SEB (1 µg/mL) stimulation. PBMC cultures were treated with SEB at 1 µg/mL for 48 hours in the presence of CD7-CD9 bispecific antibodies. The conditioned medium was collected and diluted 50-fold before analysis of the level of granzyme B using an IntelliCyt® QBead® PlexScreen. Log 2 fold changes were calculated for the MFI of granzyme B levels in the treated samples relative to the SEB stimulated controls. N=3 donors ±SEM.
Figure 11:
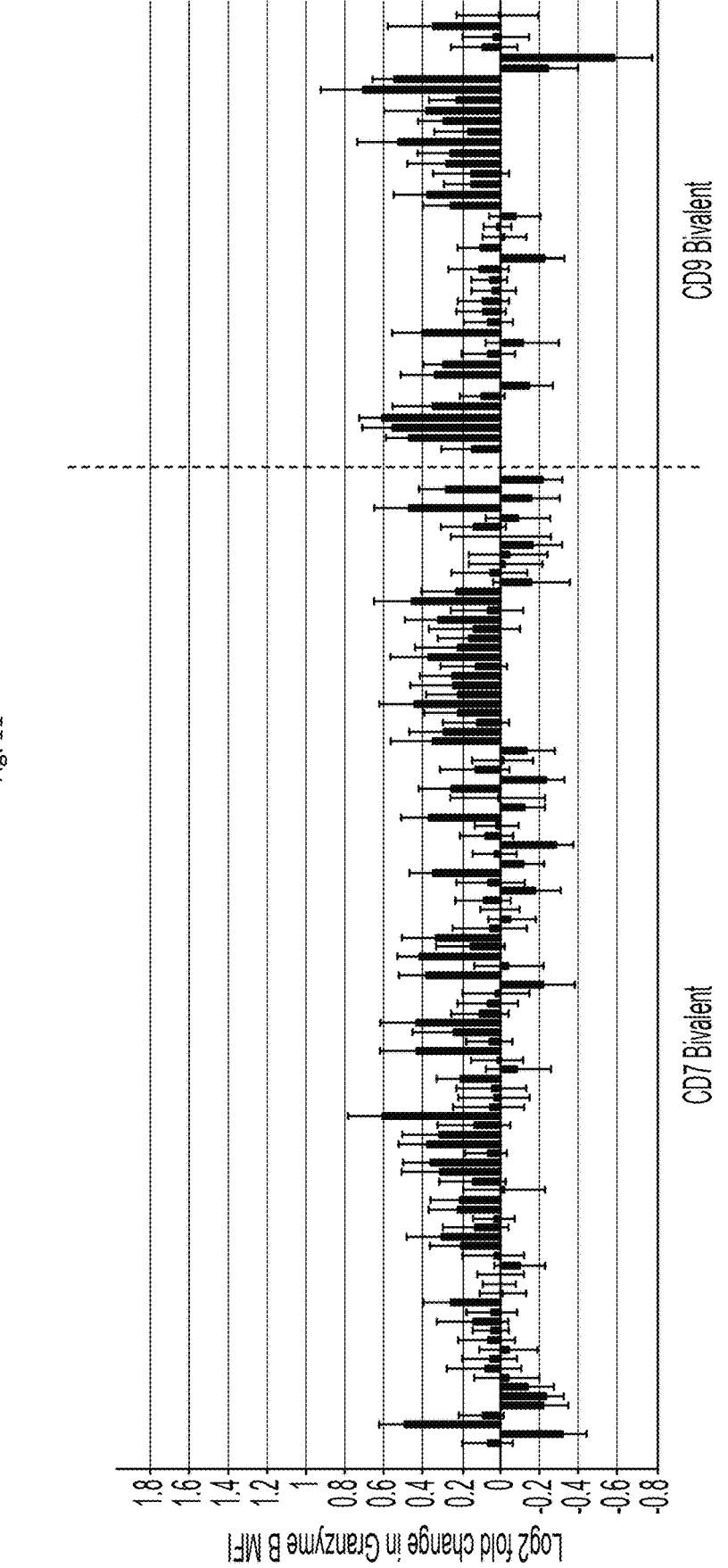
FIG. 11. Log 2 fold change in the MFI of granzyme B levels in the conditioned medium of PBMC cultures in the presence of SEB (1 µg/mL) stimulation. PBMC cultures were treated with SEB at 1 µg/mL for 48 hours in the presence of CD9 and CD7 bivalent control antibodies. The conditioned medium were collected and diluted 50-fold before analysis of the level of granzyme B using an IntelliCyt® QBead® PlexScreen. Log 2 fold changes were calculated for the MFI of granzyme B levels in the treated samples relative to the SEB stimulated controls. N=3 donors ±SEM.
Figure 12:
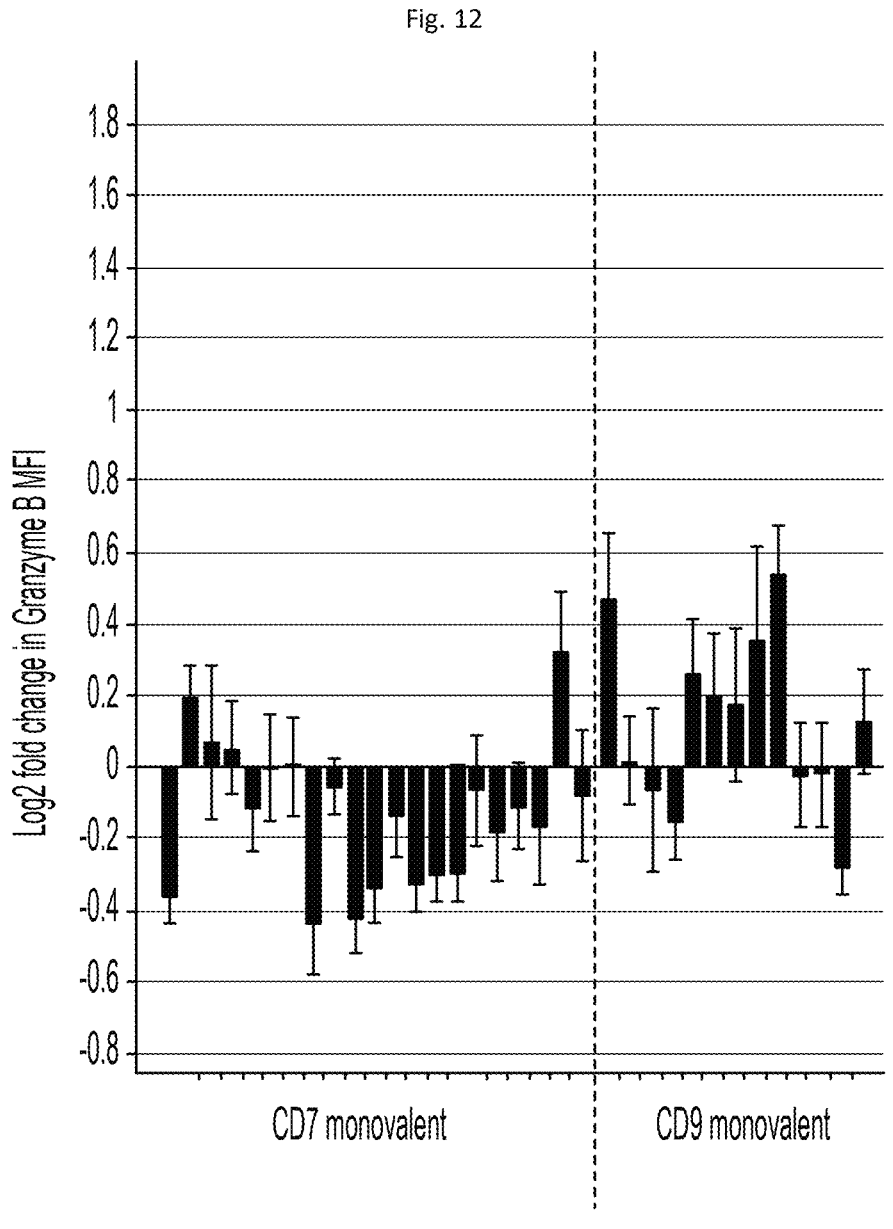
FIG. 12. Log 2 fold change in the MFI of granzyme B levels in the supernatant of PBMC cultures in the presence of SEB (1 µg/mL) stimulation. PBMC cultures were treated with SEB at 1 µg/mL for 48 hours in the presence of CD9 and CD7 monovalent control antibodies. The conditioned medium were collected and diluted 50-fold before analysis of the level of granzyme B using an IntelliCyt® QBead® PlexScreen. Log 2 fold changes were calculated for the MFI of granzyme B levels in the treated samples relative to the SEB stimulated controls. N=3 donors ±SEM.

As reported previously the CD7-CD9 bispecific antibodies led to an increase in the level of granzyme B in PBMC cultures after stimulation with SEB for 48 hours. There was no clear difference between the variable regions tested for both the anti-CD9 and anti-CD7 arms of the bispecific antibodies (FIG. 10). There was no similar increase in granzyme B detection when samples were treated with the bivalent or monovalent controls (FIGS. 11 and 12).

Example 6: CD7-CD9 Conversion to IgG Format
and Comparison of CD7-CD9 Bispecific Activity to
Ipilimumab and Nivolumab To investigate whether the Fab-X/Fab-Y bispecific antibodies against CD7 and CD9 would achieve the same effect when converted into an IgG format, the variable regions of the Fab-X and Fab-Y fusion proteins were cloned into an IgG format using established methods available in the public domain. Control IgG were also generated. The functionality of targeting CD7 and CD9 in the different bispecific formats was tested by comparing them in a SEB stimulated PBMC assay.

A grid of fusion proteins Fab-X and Fab-Y were created by diluting equimolar (1 μM) quantities of Fab-X (Fab-scFv) and Fab-Y (Fab-peptide) with specificity for CD9 and CD7 in TexMACS™ media (Miltenyi Biotec®) containing 100 U/mL penicillin/100 μg/mL streptomycin. The Fab-X and Fab-Y fusion proteins were incubated together for 1 hour (in a 37° C., 5% $CO_2$ environment), at a final concentration of 500 nM. IgG constructs, Ipilimumab (Yervoy®) and Nivolumab (Opdivo®) were diluted to 500 nM in Tex-MACS™ media containing 100 U/mL penicillin/100 μg/mL streptomycin. Negative control wells containing Tex-MACS™ media only were also generated alongside the Fab-X and Fab-Y wells.

During this time, cryopreserved human PBMC isolated from platelet leukapheresis cones were thawed and washed in TexMACS™ media and resuspended at $2.5 \times 10^6$ cells/mL. The PBMC were then seeded into 96-well U-bottom tissue culture plates (Costar) at 60 μL/well ($1.5 \times 10^5$ PBMC).

20 μL of Fab-X and Fab-Y complexes were transferred to the plates containing 60 μL PBMC. The PBMC were then either left unstimulated by the addition of 20 μL of Tex-MACS™ media or stimulated with 20 μL of SEB (1 μg/ml final concentration). This resulted in a final assay concentration of antibody treatment of 100 nM. The plates were then returned to a 37° C., 5% $CO_2$ environment for 48 hours.

After 48 hours the plates were centrifuged at 500×g for 5 minutes at 4° C. Conditioned media were transferred from the cell pellets to fresh plates and frozen at −80° C. On the day of analysis, the conditioned media were thawed and diluted 50-fold in RPMI and assayed for levels of granzyme B using an IntelliCyt® QBead® PlexScreen.

The data analysis software package ForeCyt™ (IntelliCyt®) was used to measure the median fluorescent intensity values for the granzyme B detection beads. The log 2 fold changes of granzyme B concentrations were calculated relative to control well values.

Figure 13:
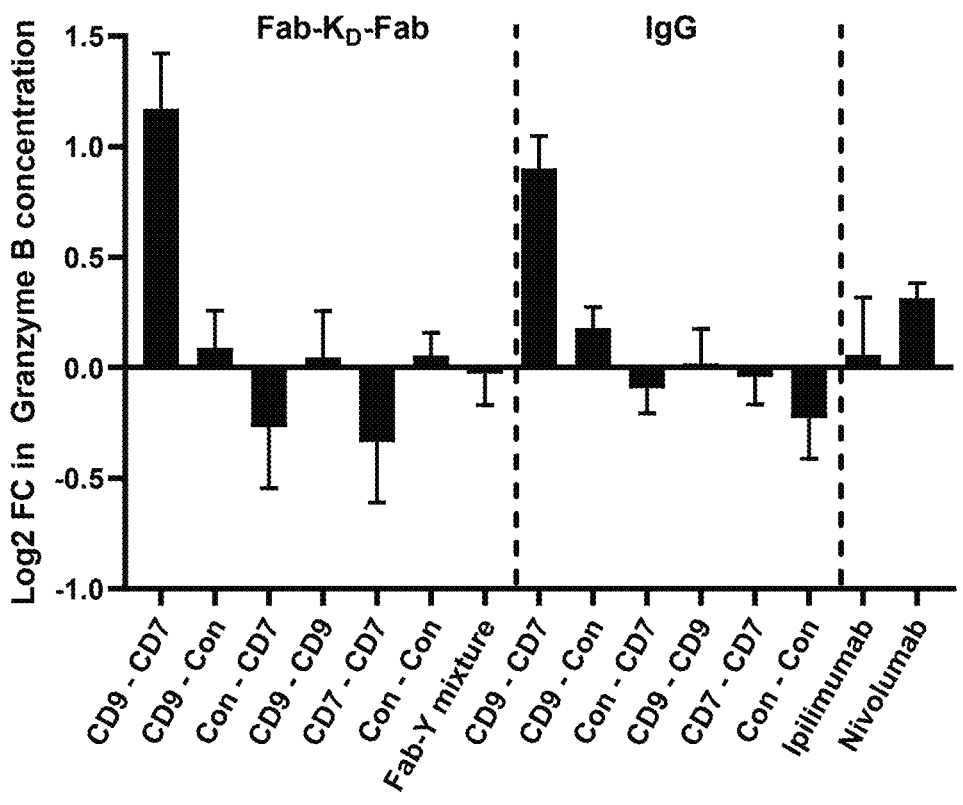
FIG. 13. Log 2 fold change in the concentration of granzyme B levels in the conditioned medium of PBMC cultures in the presence of SEB (1 µg/mL) stimulation. PBMC cultures were treated with (SEB) at 1 µg/mL for 48 hours in the presence of CD7-CD9 bispecific and control antibodies. The conditioned media were collected and diluted 50 fold before analysis of the level of granzyme B using an IntelliCyt® QBead® PlexScreen. Log 2 fold changes were calculated for the concentration of granzyme B levels in the treated samples relative to the SEB stimulated controls. N=3 donors ±SEM.

As reported previously the CD7-CD9 bispecific antibodies led to an increase in the level of granzyme B in the conditioned medium of PBMC cultures after stimulation with SEB for 48 hours (FIG. 13). There was no similar increase in granzyme B detection when samples were treated with the bivalent or monovalent controls. Furthermore, a mixture of the anti-CD9 and CD7 Fab-Y constructs did not increase granzyme B levels in the supernatant (FIG. 13). The IgG bispecific gave similar increases in granzyme B as the Fab-X/Fab-Y bispecific antibodies suggesting successful conversion to a potential therapeutic format. Furthermore, the bivalent and monovalent IgG controls did not increase granzyme B levels in the conditioned medium.

Ipilimumab (an anti-CTLA-4 antibody) was the first checkpoint inhibitor to be approved in 2011 as a treatment for melanoma, closely followed by FDA approval of the anti-PD1 directed antibody nivolumab in 2014 (Hargadon et al., International Immunopharmacol. 62:29-39 (2018)).

Whilst there are still significant challenges in understanding differences in efficacy across patient groups, ranging from complete responses, to treatment relapse and even failure to respond, (Haslam and Prasad. JAMA Network Open.5: 2e192535 (2019)), these molecules represent current clinically-validated references for immunotherapy in a range of cancer types and have been utilised in the present studies for benchmarking the activity of the novel bispecific antibodies described herein.

Neither ipilimumab nor nivolumab had an effect on the level of granzyme B in this assay, showing the superiority of an anti-CD7-CD9 bispecific antibody over the single target antibodies.

Example 7: Analysis of Anti-CD9 Antibody
Binding by Biolayer Interferometry

CD9 contains two extracellular loops: a short extracellular loop (loop 1: 34-55 in SEQ ID NO:2) and a long extracellular loop (loop 2: 112-195 in SEQ ID NO:2). We used biolayer interferometry to assess binding of our panel of CD9 Fab-Y antibodies (selected for binding to full length cell-expressed CD9) to the long extracellular loop 2 peptide using the Octet® RED384 System (FortéBio) with Anti-hIgG Fc Capture (AHC) Biosensors (FortéBio) at room temperature. Firstly, an array of 8 sensors was dipped in kinetics buffer (PBS 0.1%, BSA 0.02%, Tween 20) for 120 seconds to provide a baseline signal. Sensors were then moved to wells containing 200 μl of recombinant human CD9 long extracellular loop 2-human Fc fusion protein (10015-CD, R&D Systems®) at 2 μg/mL in kinetics buffer to immobilize the protein to the biosensor (100 seconds), followed by a second baseline step (180 seconds) in kinetics buffer to equilibrate the biosensors now coated with the CD9 long extracellular loop 2-human Fc fusion protein. No detachment of the peptide was observed during this step. Sensors were then dipped in wells containing one of the anti-CD9 Fab (10 μg/mL) to evaluate association of each antibody to CD9-loop2 (120 seconds), followed by dissociation in kinetics buffer (600 seconds). Anti-CD137 Fab-Y (11175) was used as negative control during the antibody association step. A new set of 8 biosensors was used to repeat this process for each of the anti-CD9 antibodies (7270, 7271, 7272, 7485, 7486, 7489, 7491).

As shown in Table 5, all the anti-CD9 Fab-Y antibodies tested bind to the long extracellular loop of CD9 and all are functional when combined into a Fab-X/Fab-Y bispecific antibody with anti-CD7 antibodies. A positive functional response is considered to be the capacity to increase granzyme B greater than 0.5 log 2 fold change MFI in 3 donors when added as a Fab-$K_D$-Fab with anti-CD7. (Functional data generated in example 5)

TABLE 5

| | CD9 long extracellular loop 2 | Functional (Y/N) |
|---|---|---|
| 7270 | ✓ | Y |
| 7271 | ✓ | Y |
| 7272 | ✓ | Y |
| 7485 | ✓ | Y |
| 7486 | ✓ | Y |
| 7489 | ✓ | Y |
| 7491 | ✓ | Y |

The invention claimed is:

1. An antibody which comprises a first antigen-binding portion binding CD7 and a second antigen-binding portion binding CD9, wherein the first antigen-binding portion binding CD7 comprises a first heavy chain variable region and a first light chain variable region, wherein the second antigen-binding portion binding CD9 comprises a second heavy chain variable region and a second light chain variable region, and wherein:

a. the first heavy chain variable region comprises a CDR-H1 comprising SEQ ID NO: 3, a CDR-H2 comprising SEQ ID NO: 4 and a CDR-H3 comprising SEQ ID NO: 5; and b. the first light chain variable region comprises a CDR-L1 comprising SEQ ID NO: 6, a CDR-L2 comprising SEQ ID NO: 7 and a CDR-L3 comprising SEQ ID NO: 8; and c. the second heavy chain variable region comprises a CDR-H1 comprising SEQ ID NO: 9, a CDR-H2 comprising SEQ ID NO: 10 and a CDR-H3 comprising SEQ ID NO: 11; and d. the second light chain variable region comprises a CDR-L1 comprising SEQ ID NO: 12, a CDR-L2 comprising SEQ ID NO: 13 and a CDR-L3 comprising SEQ ID NO: 14.

2. The antibody according to claim 1, wherein each of the antigen-binding portions is a monoclonal antigen-binding portion.

3. The antibody according to claim 1, wherein each of the antigen-binding portions is independently selected from a Fab, a Fab', or a scFv.

4. The antibody according to claim 1, wherein the antigen-binding portions are the antigen-binding portions of an IgG.

5. The antibody according to claim 1, wherein the antibody comprises a heavy chain constant region selected from an IgG1, an IgG2, an IgG3 or an IgG4 isotype, or a variant thereof.

6. The antibody according to claim 1, wherein the antibody further comprises at least an additional antigen-binding portion.

7. The antibody according to claim 6, wherein the additional antigen-binding portion increases the half-life of the antibody.

8. The antibody according to claim 7, wherein the additional antigen-binding portion binds albumin.

9. The antibody according to claim 1, wherein:

a. the first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21; or b. the first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

10. A pharmaceutical composition comprising the antibody according to claim 1 and one or more pharmaceutically acceptable excipients.

11. A method of treating a subject afflicted with cancer, an infectious disease, or combinations thereof comprising administering to the subject a pharmaceutically effective amount of the antibody according to claim 1 or a pharmaceutical composition comprising the antibody and one or more pharmaceutically acceptable excipients.

12. The method according to claim 11, wherein the antibody or the composition is administered concomitantly or sequentially to one or more additional cancer therapies.

13. The method according to claim 11, wherein the antibody promotes NK cell activity.

14. The method according to claim 11, wherein the subject is afflicted with cancer.

15. The method according to claim 11, wherein the pharmaceutical composition promotes NK cell activity.

* * * * *

SEQUENCE LISTING

<160> NUMBER OF SEQ ID NOS: 22

<210> SEQ ID NO 1
<211> LENGTH: 240
<212> TYPE: PRT
<213> ORGANISM: Homo sapiens

<400> SEQUENCE: 1

```
Met Ala Gly Pro Pro Arg Leu Leu Leu Leu Pro Leu Leu Leu Ala Leu
1               5                   10                  15

Ala Arg Gly Leu Pro Gly Ala Leu Ala Ala Gln Glu Val Gln Gln Ser
            20                  25                  30

Pro His Cys Thr Thr Val Pro Val Gly Ala Ser Val Asn Ile Thr Cys
        35                  40                  45

Ser Thr Ser Gly Gly Leu Arg Gly Ile Tyr Leu Arg Gln Leu Gly Pro
    50                  55                  60

Gln Pro Gln Asp Ile Ile Tyr Tyr Glu Asp Gly Val Val Pro Thr Thr
65                  70                  75                  80

Asp Arg Arg Phe Arg Gly Arg Ile Asp Phe Ser Gly Ser Gln Asp Asn
                85                  90                  95

Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
            115                 120                 125

Val Leu Val Thr Glu Glu Gln Ser Gln Gly Trp His Arg Cys Ser Asp
    130                 135                 140

Ala Pro Pro Arg Ala Ser Ala Leu Pro Ala Pro Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
            195                 200                 205

Cys Ser Trp Arg Asp Lys Asn Ser Ala Ala Cys Val Val Tyr Glu Asp
    210                 215                 220

Met Ser His Ser Arg Cys Asn Thr Leu Ser Ser Pro Asn Gln Tyr Gln
225                 230                 235                 240
```

<210> SEQ ID NO 2
<211> LENGTH: 228
<212> TYPE: PRT
<213> ORGANISM: Homo sapiens

<400> SEQUENCE: 2

```
Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
```

-continued

```
                    85              90              95
Leu Val Ile Phe Ala Ile Glu Ile Ala Ala Ala Ile Trp Gly Tyr Ser
            100             105             110

His Lys Asp Glu Val Ile Lys Glu Val Gln Glu Phe Tyr Lys Asp Thr
            115             120             125

Tyr Asn Lys Leu Lys Thr Lys Asp Glu Pro Gln Arg Glu Thr Leu Lys
    130             135             140

Ala Ile His Tyr Ala Leu Asn Cys Cys Gly Leu Ala Gly Gly Val Glu
145             150             155             160

Gln Phe Ile Ser Asp Ile Cys Pro Lys Lys Asp Val Leu Glu Thr Phe
                165             170             175

Thr Val Lys Ser Cys Pro Asp Ala Ile Lys Glu Val Phe Asp Asn Lys
            180             185             190

Phe His Ile Ile Gly Ala Val Gly Ile Gly Ile Ala Val Val Met Ile
            195             200             205

Phe Gly Met Ile Phe Ser Met Ile Leu Cys Cys Ala Ile Arg Arg Asn
    210             215             220

Arg Glu Met Val
225

<210> SEQ ID NO 3
<211> LENGTH: 10
<212> TYPE: PRT
<213> ORGANISM: Artificial Sequence
<220> FEATURE:
<223> OTHER INFORMATION: CDR-H1 VR8850

<400> SEQUENCE: 3

Gly Phe Ser Leu Ser Ser Phe Ala Met Cys
1               5               10

<210> SEQ ID NO 4
<211> LENGTH: 16
<212> TYPE: PRT
<213> ORGANISM: Artificial Sequence
<220> FEATURE:
<223> OTHER INFORMATION: CDR-H2 VR8850

<400> SEQUENCE: 4

Ile Ile Asn Thr Gly Gly Ser Ala Tyr Tyr Ala Ser Trp Ala Thr Gly
1               5               10              15

<210> SEQ ID NO 5
<211> LENGTH: 14
<212> TYPE: PRT
<213> ORGANISM: Artificial Sequence
<220> FEATURE:
<223> OTHER INFORMATION: CDR-H3 VR8850

<400> SEQUENCE: 5

Gly Asn Gly Tyr Ala Gly Tyr Gly Tyr Asp Gly Phe Asp Pro
1               5               10

<210> SEQ ID NO 6
<211> LENGTH: 11
<212> TYPE: PRT
<213> ORGANISM: Artificial Sequence
<220> FEATURE:
<223> OTHER INFORMATION: CDR-L1 VR8850

<400> SEQUENCE: 6

Gln Ala Ser Gln Ser Ile Thr Ser Trp Leu Ser
```

1               5               10

<210> SEQ ID NO 7
<211> LENGTH: 7
<212> TYPE: PRT
<213> ORGANISM: Artificial Sequence
<220> FEATURE:
<223> OTHER INFORMATION: CDR-L2 VR8850

<400> SEQUENCE: 7

Ala Ala Ser Lys Leu Thr Phe
1               5

<210> SEQ ID NO 8
<211> LENGTH: 12
<212> TYPE: PRT
<213> ORGANISM: Artificial Sequence
<220> FEATURE:
<223> OTHER INFORMATION: CDR-L3 VR8850

<400> SEQUENCE: 8

Gln Ser Asn Tyr Gly Ser Ser Ser Ala Tyr Gly Ala
1               5               10

<210> SEQ ID NO 9
<211> LENGTH: 10
<212> TYPE: PRT
<213> ORGANISM: Artificial Sequence
<220> FEATURE:
<223> OTHER INFORMATION: CDR-H1 VR7272

<400> SEQUENCE: 9

Gly Phe Ser Leu Ser Ser Tyr Ala Met Gly
1               5               10

<210> SEQ ID NO 10
<211> LENGTH: 16
<212> TYPE: PRT
<213> ORGANISM: Artificial Sequence
<220> FEATURE:
<223> OTHER INFORMATION: CDR-H2 VR7272

<400> SEQUENCE: 10

Ala Ile Gly Ser Ile Thr Ala Thr Gly Tyr Ala Arg Trp Ala Lys Gly
1               5               10              15

<210> SEQ ID NO 11
<211> LENGTH: 12
<212> TYPE: PRT
<213> ORGANISM: Artificial Sequence
<220> FEATURE:
<223> OTHER INFORMATION: CDR-H3 VR7272

<400> SEQUENCE: 11

Glu Ile Tyr Val Gly Ser Ala Tyr Ala Phe Asp Ile
1               5               10

<210> SEQ ID NO 12
<211> LENGTH: 11
<212> TYPE: PRT
<213> ORGANISM: Artificial Sequence
<220> FEATURE:
<223> OTHER INFORMATION: CDR-L1 VR7272

<400> SEQUENCE: 12

Gln Ala Ser Gln Ser Ile Ser Asn Tyr Leu Ala
1               5               10

```
<210> SEQ ID NO 13
<211> LENGTH: 7
<212> TYPE: PRT
<213> ORGANISM: Artificial Sequence
<220> FEATURE:
<223> OTHER INFORMATION: CDR-L2 VR7272

<400> SEQUENCE: 13

Leu Ala Ser Thr Leu Ala Ser
1               5

<210> SEQ ID NO 14
<211> LENGTH: 11
<212> TYPE: PRT
<213> ORGANISM: Artificial Sequence
<220> FEATURE:
<223> OTHER INFORMATION: CDR-L3 VR7272

<400> SEQUENCE: 14

Gln Gln Gly Tyr Ile Asp Asn Val Asn Lys Gly
1               5                   10

<210> SEQ ID NO 15
<211> LENGTH: 119
<212> TYPE: PRT
<213> ORGANISM: Artificial Sequence
<220> FEATURE:
<223> OTHER INFORMATION: VH VR8850

<400> SEQUENCE: 15

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Phe Ala
            20                  25                  30

Met Cys Trp Val Arg Gln Ala Pro Gly Lys Gly Leu Glu Tyr Ile Gly
        35                  40                  45

Ile Ile Asn Thr Gly Gly Ser Ala Tyr Tyr Ala Ser Trp Ala Thr Gly
    50                  55                  60

Arg Phe Thr Ile Ser Lys Thr Ser Thr Thr Val Asp Leu Lys Ile Ser
65                  70                  75                  80

Ser Pro Thr Thr Glu Asp Thr Ala Thr Tyr Phe Cys Ala Arg Gly Asn
                85                  90                  95

Gly Tyr Ala Gly Tyr Gly Tyr Asp Gly Phe Asp Pro Trp Gly Pro Gly
            100                 105                 110

Thr Leu Val Thr Val Ser Ser
        115

<210> SEQ ID NO 16
<211> LENGTH: 430
<212> TYPE: DNA
<213> ORGANISM: Artificial Sequence
<220> FEATURE:
<223> OTHER INFORMATION: VH nucl VR8850

<400> SEQUENCE: 16
aagcttcgaa gccaccatgg agactgggct gcgctggctt ctcctggtcg ctgtgctcaa      60
aggtgtccag tgtcagtcgg tggaggagtc cggggggtcgc ctggtcacgc cggggacacc     120
cctgacactc acctgcacag tctctggatt ctccctcagt agctttgcaa tgtgctgggt     180
ccgccaggct ccagggaagg gactggaata catcggaatc attaatactg gtggtagcgc     240
```

-continued

```
atactacgcg agctgggcga caggccgatt caccatctcc aaaacctcga ccacggtgga      300
tctgaaaatc tccagtccga caaccgagga cacggccacc tatttctgtg ccagaggaaa      360
tggttatgct ggttatggtt atgatggttt tgatccctgg ggcccaggca ccctggtcac      420
cgtctcgagt                                                             430
```

```
<210> SEQ ID NO 17
<211> LENGTH: 110
<212> TYPE: PRT
<213> ORGANISM: Artificial Sequence
<220> FEATURE:
<223> OTHER INFORMATION: VL VR8850

<400> SEQUENCE: 17

Asp Ile Val Met Thr Gln Thr Pro Ala Ser Val Ser Glu Pro Val Gly
1               5                   10                  15

Gly Thr Val Thr Ile Lys Cys Gln Ala Ser Gln Ser Ile Thr Ser Trp
            20                  25                  30

Leu Ser Trp Tyr Gln Gln Lys Pro Gly Gln Pro Pro Lys Leu Leu Ile
        35                  40                  45

Tyr Ala Ala Ser Lys Leu Thr Phe Gly Val Ser Ser Arg Phe Arg Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Asn Tyr Gly Ser Ser Ser
                85                  90                  95

Ala Tyr Gly Ala Phe Gly Gly Gly Thr Glu Val Val Val Lys
            100                 105                 110
```

```
<210> SEQ ID NO 18
<211> LENGTH: 421
<212> TYPE: DNA
<213> ORGANISM: Artificial Sequence
<220> FEATURE:
<223> OTHER INFORMATION: VL nucl VR8850

<400> SEQUENCE: 18
aagcttcgaa gccaccatgg acacgagggc ccccactcag ctgctggggc tcctgctgct       60
ctggctccca ggtgccagat gtgctgacat tgtgatgacc cagactccag cctccgtgtc      120
tgaacctgtg ggaggcacag tcaccatcaa gtgccaggcc agtcagagca ttaccagttg      180
gttatcctgg tatcagcaga aaccagggca gcctcccaag ctcctgatct acgcggcatc      240
caaactgaca tttggggtct catcaagatt cagaggcagt ggatctggga cagagtacac      300
tctcaccatc agcgacctgg agtgtgccga tgctgccact tactactgtc aaagcaatta      360
tggtagtagt agtgcttatg gggctttcgg cggaggacc gaggtggtgg tcaaacgtac       420
g                                                                      421
```

```
<210> SEQ ID NO 19
<211> LENGTH: 117
<212> TYPE: PRT
<213> ORGANISM: Artificial Sequence
<220> FEATURE:
<223> OTHER INFORMATION: VH VR7272

<400> SEQUENCE: 19

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
```

-continued

```
                20              25              30

Met Gly Trp Val Arg Gln Ala Pro Gly Lys Gly Leu Glu Trp Ile Gly
        35              40              45

Ala Ile Gly Ser Ile Thr Ala Thr Gly Tyr Ala Arg Trp Ala Lys Gly
    50              55              60

Arg Phe Ser Ile Ser Lys Thr Ser Thr Thr Val Asp Leu Lys Met Thr
65              70              75              80

Ser Pro Thr Thr Glu Asp Thr Ala Thr Tyr Phe Cys Ala Arg Glu Ile
                85              90              95

Tyr Val Gly Ser Ala Tyr Ala Phe Asp Ile Trp Gly Pro Gly Thr Leu
                100             105             110

Val Thr Val Ser Ser
        115
```

<210> SEQ ID NO 20
<211> LENGTH: 424
<212> TYPE: DNA
<213> ORGANISM: Artificial Sequence
<220> FEATURE:
<223> OTHER INFORMATION: VH nucl VR7272

<400> SEQUENCE: 20

```
aagcttcgaa gccaccatgg agactgggct gcgctggctt ctcctggtcg ctgtgctcaa      60
aggtgtccag tgtcagtcgc tggaggagtc cggggggtcgc ctggtcacgc ctgggacacc     120
cctgacactc acctgcacag tctctggatt ctccctcagt agctatgcaa tgggctgggt     180
ccgccaggct ccagggaagg ggctggagtg gatcggagcc attggtagta ttactgccac     240
tggctacgcg cgctgggcaa aaggccgatt cagcatctcc aagacctcga ccacggtgga     300
tctgaaaatg accagtccga caaccgagga cacggccacc tatttctgtg ccagagagat     360
ttatgttggg tctgcttatg cctttgacat ctggggccca ggcaccctgg tcaccgtctc     420
gagt                                                                  424
```

<210> SEQ ID NO 21
<211> LENGTH: 109
<212> TYPE: PRT
<213> ORGANISM: Artificial Sequence
<220> FEATURE:
<223> OTHER INFORMATION: VL VR7272

<400> SEQUENCE: 21

```
Ala Tyr Asp Met Thr Gln Thr Pro Ala Ser Val Glu Val Ala Val Gly
1               5               10              15

Asp Thr Val Thr Ile Lys Cys Gln Ala Ser Gln Ser Ile Ser Asn Tyr
                20              25              30

Leu Ala Trp Tyr Gln Gln Lys Pro Gly Gln Pro Pro Lys Leu Leu Ile
        35              40              45

Tyr Leu Ala Ser Thr Leu Ala Ser Gly Val Pro Ser Arg Phe Lys Gly
    50              55              60

Ser Gly Ser Gly Thr Glu Phe Thr Leu Thr Ile Ser Asp Leu Glu Cys
65              70              75              80

Ala Asp Ala Ala Thr Tyr Tyr Cys Gln Gln Gly Tyr Ile Asp Asn Val
                85              90              95

Asn Lys Gly Phe Gly Gly Gly Thr Glu Val Val Val Lys
            100             105
```

<210> SEQ ID NO 22

-continued

```
<211> LENGTH: 415
<212> TYPE: DNA
<213> ORGANISM: Artificial Sequence
<220> FEATURE:
<223> OTHER INFORMATION: VL nucl VR7272

<400> SEQUENCE: 22
aagcttcgaa gccaccatgg acacgagggc ccccactcag ctgctggggc tcctgctgct      60
ctggctccca ggtgccagat gtgcctatga tatgacccag actccagcct ctgtggaggt     120
agctgtggga gacactgtca ccatcaagtg tcaggccagt cagagcatta gtaactactt     180
agcctggtat cagcagaaac cagggcagcc tcccaagctc ctgatctatc tggcatctac     240
tctggcatct ggggtcccat cgcggttcaa aggcagtgga tctgggacag agttcactct     300
caccatcagc gacctggagt gtgccgatgc tgccacttac tattgtcaac agggttatat     360
tgataatgtt aataaaggtt tcggcggagg gaccgaggtg gtggtcaaac gtacg          415
```